(12) United States Patent
Kremmidiotis et al.

(10) Patent No.: US 10,564,162 B2
(45) Date of Patent: Feb. 18, 2020

(54) PREDICTIVE BIOMARKERS

(71) Applicant: BIONOMICS LIMITED, Thebarton, South Australia (AU)

(72) Inventors: Gabriel Kremmidiotis, Flagstaff Hill (AU); Annabell Francis Leske, Allenby Gardens (AU)

(73) Assignee: BIONOMICS LIMITED, Thebarton, South Australia (AU)

( * ) Notice: Subject to any disclaimer, the term of this patent is extended or adjusted under 35 U.S.C. 154(b) by 75 days.

(21) Appl. No.: 15/322,845

(22) PCT Filed: Jul. 2, 2015

(86) PCT No.: PCT/AU2015/000387
§ 371 (c)(1),
(2) Date: Dec. 29, 2016

(87) PCT Pub. No.: WO2016/000028
PCT Pub. Date: Jan. 7, 2016

(65) Prior Publication Data
US 2018/0196048 A1    Jul. 12, 2018

(30) Foreign Application Priority Data
Jul. 2, 2014    (AU) ............................. 2014902541

(51) Int. Cl.
| | |
|---|---|
| *G01N 33/574* | (2006.01) |
| *A61K 45/06* | (2006.01) |
| *A61K 31/343* | (2006.01) |
| *A61P 35/00* | (2006.01) |

(52) U.S. Cl.
CPC ......... *G01N 33/574* (2013.01); *A61K 31/343* (2013.01); *A61K 45/06* (2013.01); *A61P 35/00* (2018.01); *G01N 2333/475* (2013.01); *G01N 2333/805* (2013.01); *G01N 2333/96494* (2013.01); *G01N 2800/52* (2013.01)

(58) Field of Classification Search
None
See application file for complete search history.

(56) References Cited

U.S. PATENT DOCUMENTS 6,607,894 B1 * 8/2003 Lopata ............. G01N 33/57442
435/188
2006/0111398 A1 * 5/2006 Fourie ................. A61K 31/4709
514/312

FOREIGN PATENT DOCUMENTS

WO    WO-2004083108 A1 *  9/2004 ........ B01L 3/502746
WO    WO-2007087684 A1 *  8/2007 ........... C07D 209/12

OTHER PUBLICATIONS

Itoh et al, Clinical and Experimental Metastasis, 1999, vol. 17, pp. 177-181 (Year: 1999).*
The abstract of Cai (Frontiers in Anti-Cancer Drug Discovery, 2010, vol. 1, pp. 380-427) (Year: 2010).*
Sarantopoulos, J., et al., "A phase I/II trial of BNC105P with everolimus in metastatic renal cell carcinoma (mRCC) patients: updated phase I results of the DisrupTOR-1 trial (Hoosier Oncology Group)," American Society for Clinical Oncology (ASCO) 2013 Annual Meeting, May 31-Jun. 4, 2013, Chicago, Illinois, USA, Abstract ID 4563 and associated poster [retrieved from internet on Jul. 8, 2015] URL: <http://meetinglibrary.asco.org/content/107981-132>.
Farace, F., et al., "Identification of biomarkers of vascular disrupting agent activity during AVE8062 phase I trials in solid tumors," Cancer Research, 2009, vol. 69, American Association for Cancer Research (AACR) Annual Meeting, Apr. 18-22, 2009, Denver, Colorado, USA, Abstract 5441 [retrieved from internet on Jul. 8, 2015] URL <http:/ /cancerres.aacrjournals.org/content/69/9_Supplement/5441.short>.
Sessa, C., et al., "Phase I safety, pharmacokinetic and pharmacodynamic evaluation of the vascular disrupting agent ombrabulin (AVE8062) in patients with advanced solid tumors," Clinical Cancer Research, 2013, vol. 19, pp. 4832-4842.
Verwey, N. A., et al., "Serum amyloid P component as a biomarker in mild cognitive impairment and Alzheimer's disease," Dementia and Geriatric Cognitive Disorders, 2008, vol. 26, pp. 522-527.
Myoglobin ELISA kit product information ALPCO Diagnostics, Nov. 11, 2009 [retrieved from internet on Aug. 18, 2015] URL: https://www.alpco.com/pdfs/24/24-MYOHU-E01.pdf.
Stem Cell Factor ELISA kit product information Cloud-Clone Corp, Jul. 2013 [retrieved from internet on Aug. 18, 2015] URL: <http://www.uscnk.com/manual/ELISA-Kit-for-Stem-Cell-Factor-(SCF)-E90120Mu.pdf>.
Sex Hormone Binding Globulin ELISA kit product information Cloud-Clone Corp, Jul. 2013 [retrieved from internet on Aug. 18, 2015] URL: http://www.uscnk.com/manual/ELISA-Kit-for-Sex-Hormone-Binding-Globulin-(SHBG)-E90396Ra.pdf.
Extended European Search Report for European Patent Application No. 15814255.4, dated Mar. 19, 2018, 10 pages.

* cited by examiner

*Primary Examiner* — Karen A. Canella
(74) *Attorney, Agent, or Firm* — Finnegan, Henderson, Farabow, Garrett & Dunner, LLP

(57) ABSTRACT

The present disclosure relates to the biological markers SAP, SHBG, Myoglobin, MMP-9, and SCF that are predictive for patient response to treatment with a vascular disrupting agent. In particular, the present disclosure relates to biological markers predictive for cancer patient response to treatment with a vascular disrupting agent, as well as methods of treating a cancer patient with a vascular disrupting agent.

9 Claims, 6 Drawing Sheets

Specification includes a Sequence Listing.

SEQUENCE LISTING

```
<160> NUMBER OF SEQ ID NOS: 5

<210> SEQ ID NO 1
<211> LENGTH: 223
<212> TYPE: PRT
<213> ORGANISM: Homo sapiens

<400> SEQUENCE: 1

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
            20                  25                  30

Glu Ser Val Thr Asp His Val Asn Leu Ile Thr Pro Leu Glu Lys Pro
        35                  40                  45

Leu Gln Asn Phe Thr Leu Cys Phe Arg Ala Tyr Ser Asp Leu Ser Arg
    50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Ser Gly Ile Ala Glu Phe Trp Ile
        115                 120                 125

Asn Gly Thr Pro Leu Val Lys Lys Gly Leu Arg Gln Gly Tyr Phe Val
    130                 135                 140

Glu Ala Gln Pro Lys Ile Val Leu Gly Gln Glu Gln Asp Ser Tyr Gly
145                 150                 155                 160
```

```
Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
        195                 200                 205

Tyr Glu Ile Arg Gly Tyr Val Ile Ile Lys Pro Leu Val Trp Val
    210                 215                 220

<210> SEQ ID NO 2
<211> LENGTH: 402
<212> TYPE: PRT
<213> ORGANISM: Homo sapiens

<400> SEQUENCE: 2

Met Glu Ser Arg Gly Pro Leu Ala Thr Ser Arg Leu Leu Leu Leu Leu
1               5                   10                  15

Leu Leu Leu Leu Arg His Thr Arg Gln Gly Trp Ala Leu Arg Pro
            20                  25                  30

Val Leu Pro Thr Gln Ser Ala His Asp Pro Pro Ala Val His Leu Ser
        35                  40                  45

Asn Gly Pro Gly Gln Glu Pro Ile Ala Val Met Thr Phe Asp Leu Thr
    50                  55                  60

Lys Ile Thr Lys Thr Ser Ser Phe Glu Val Arg Thr Trp Asp Pro
65                  70                  75                  80

Glu Gly Val Ile Phe Tyr Gly Asp Thr Asn Pro Lys Asp Asp Trp Phe
                85                  90                  95

Met Leu Gly Leu Arg Asp Gly Arg Pro Glu Ile Gln Leu His Asn His
            100                 105                 110

Trp Ala Gln Leu Thr Val Gly Ala Gly Pro Arg Leu Asp Asp Gly Arg
        115                 120                 125

Trp His Gln Val Glu Val Lys Met Glu Gly Asp Ser Val Leu Leu Glu
    130                 135                 140

Val Asp Gly Glu Glu Val Leu Arg Leu Arg Gln Val Ser Gly Pro Leu
145                 150                 155                 160

Thr Ser Lys Arg His Pro Ile Met Arg Ile Ala Leu Gly Gly Leu Leu
                165                 170                 175

Phe Pro Ala Ser Asn Leu Arg Leu Pro Leu Val Pro Ala Leu Asp Gly
            180                 185                 190

Cys Leu Arg Arg Asp Ser Trp Leu Asp Lys Gln Ala Glu Ile Ser Ala
        195                 200                 205

Ser Ala Pro Thr Ser Leu Arg Ser Cys Asp Val Glu Ser Asn Pro Gly
    210                 215                 220

Ile Phe Leu Pro Pro Gly Thr Gln Ala Glu Phe Asn Leu Arg Asp Ile
225                 230                 235                 240

Pro Gln Pro His Ala Glu Pro Trp Ala Phe Ser Leu Asp Leu Gly Leu
                245                 250                 255

Lys Gln Ala Ala Gly Ser Gly His Leu Leu Ala Leu Gly Thr Pro Glu
            260                 265                 270

Asn Pro Ser Trp Leu Ser Leu His Leu Gln Asp Gln Lys Val Val Leu
        275                 280                 285

Ser Ser Gly Ser Gly Pro Gly Leu Asp Leu Pro Leu Val Leu Gly Leu
    290                 295                 300

Pro Leu Gln Leu Lys Leu Ser Met Ser Arg Val Val Leu Ser Gln Gly
```

305                 310                 315                 320

Ser Lys Met Lys Ala Leu Ala Leu Pro Pro Leu Gly Leu Ala Pro Leu
                325                 330                 335

Leu Asn Leu Trp Ala Lys Pro Gln Gly Arg Leu Phe Leu Gly Ala Leu
                340                 345                 350

Pro Gly Glu Asp Ser Ser Thr Ser Phe Cys Leu Asn Gly Leu Trp Ala
                355                 360                 365

Gln Gly Gln Arg Leu Asp Val Asp Gln Ala Leu Asn Arg Ser His Glu
            370                 375                 380

Ile Trp Thr His Ser Cys Pro Gln Ser Pro Gly Asn Gly Thr Asp Ala
385                 390                 395                 400

Ser His

<210> SEQ ID NO 3
<211> LENGTH: 154
<212> TYPE: PRT
<213> ORGANISM: Homo sapiens

<400> SEQUENCE: 3

Met Gly Leu Ser Asp Gly Glu Trp Gln Leu Val Leu Asn Val Trp Gly
1               5                   10                  15

Lys Val Glu Ala Asp Ile Pro Gly His Gly Gln Glu Val Leu Ile Arg
                20                  25                  30

Leu Phe Lys Gly His Pro Glu Thr Leu Glu Lys Phe Asp Lys Phe Lys
            35                  40                  45

His Leu Lys Ser Glu Asp Glu Met Lys Ala Ser Glu Asp Leu Lys Lys
        50                  55                  60

His Gly Ala Thr Val Leu Thr Ala Leu Gly Gly Ile Leu Lys Lys Lys
65                  70                  75                  80

Gly His His Glu Ala Glu Ile Lys Pro Leu Ala Gln Ser His Ala Thr
                85                  90                  95

Lys His Lys Ile Pro Val Lys Tyr Leu Glu Phe Ile Ser Glu Cys Ile
                100                 105                 110

Ile Gln Val Leu Gln Ser Lys His Pro Gly Asp Phe Gly Ala Asp Ala
            115                 120                 125

Gln Gly Ala Met Asn Lys Ala Leu Glu Leu Phe Arg Lys Asp Met Ala
        130                 135                 140

Ser Asn Tyr Lys Glu Leu Gly Phe Gln Gly
145                 150

<210> SEQ ID NO 4
<211> LENGTH: 707
<212> TYPE: PRT
<213> ORGANISM: Homo sapiens

<400> SEQUENCE: 4

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Leu Gln Lys Gln Leu Ser Leu
65                  70                  75                  80

-continued

```
Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430

Lys Asp Asp Val Asn Gly Ile Arg His Leu Tyr Gly Pro Arg Pro Glu
        435                 440                 445

Pro Glu Pro Arg Pro Pro Thr Thr Thr Pro Gln Pro Thr Ala Pro
    450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495
```

Pro Thr Ala Gly Pro Ser Thr Ala Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
        530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590

Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

<210> SEQ ID NO 5
<211> LENGTH: 273
<212> TYPE: PRT
<213> ORGANISM: Homo sapiens

<400> SEQUENCE: 5

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

```
Ser Asp Cys Val Val Ser Ser Thr Leu Ser Pro Glu Lys Asp Ser Arg
            165             170             175

Val Ser Val Thr Lys Pro Phe Met Leu Pro Pro Val Ala Ala Ser Ser
            180             185             190

Leu Arg Asn Asp Ser Ser Ser Asn Arg Lys Ala Lys Asn Pro Pro
        195             200             205

Gly Asp Ser Ser Leu His Trp Ala Ala Met Ala Leu Pro Ala Leu Phe
        210             215             220

Ser Leu Ile Ile Gly Phe Ala Phe Gly Ala Leu Tyr Trp Lys Lys Arg
225             230             235             240

Gln Pro Ser Leu Thr Arg Ala Val Glu Asn Ile Gln Ile Asn Glu Glu
            245             250             255

Asp Asn Glu Ile Ser Met Leu Gln Glu Lys Glu Arg Glu Phe Gln Glu
            260             265             270

Val
```

PREDICTIVE BIOMARKERS

CROSS-REFERENCE TO RELATED APPLICATIONS

This application is a national phase application of International Application No. PCT/AU2015/000387, filed Jul. 2, 2015, and claims the priority of Australian Application No. 2014902541, filed Jul. 2, 2014, the content of both of which is incorporated herein by reference.

FIELD

The present invention relates to biological markers that are predictive for patient response to treatment with a vascular disrupting agent. In particular, the present invention relates to biological markers predictive for cancer patient response to treatment with a vascular disrupting agent, as well as methods of treating a cancer patient with a vascular disrupting agent.

BACKGROUND

Endothelial cells are highly dependent on tubulin cytoskeleton for their motility, invasion, attachment, alignment and proliferation. Vascular disrupting agents (VDAs), a new class of agents, target endothelial cells and pericytes of the already established tumor vasculature. Most VDAs induce changes in endothelial cell shape by disruption of the cytoskeleton and cell-to-cell junctions. This results in increased permeability to proteins and an increased interstitial fluid pressure, which might be sufficient to reduce vessel diameter. Plasma leakage also leads to increased blood viscosity resulting in decreased blood flow and rouleaux formation. Another factor contributing to the vascular shutdown is the activation of platelets through contact with basement membrane components, which are exposed. All together this cascade of events results in vascular shutdown more selectively in tumor endothelium than normal endothelium. It is suggested that the inhibition of blood flow and the subsequent compromised supply of oxygen and nutrients will induce necrosis of many tumor cells downstream.

Vascular disrupting agents have been divided into two types, small molecule and ligand directed VDAs. Small molecule VDAs are in a more advanced stage of clinical development. Small molecule VDAs are either tubulin-binding agents or flavonoids. Tubulin-binding agents work by acting at the colchicine-binding site of the β-subunit of endothelial tubulin, resulting in depolymerization of microtubules and disorganization of actin and tubulin (e.g. combretastatin). Disruption of the endothelial cytoskeleton results in conformational changes leading to loss of blood flow. Tumor-related endothelial cells are much more sensitive to the activity of tubulin-binding agents than normal endothelial cells.

Clinical studies investigating the efficacy of VDAs, however, have not been able to meet objectives for increases in overall survival or 6 month progression free survival across patient populations.

SUMMARY

The present inventors have analysed the level of biological markers in patients prior to and following infusion of a vascular disrupting agent and found that changes in the pre- to post-administration levels of certain biological markers are indicative of the patient responding to treatment with the vascular disrupting agent.

Accordingly, in a first aspect there is provided a method for predicting a response to treatment with a vascular disrupting agent in a patient, the method comprising:

identifying a patient having a level of a biological marker prior to administration with the vascular disrupting agent which is different to the level of the biological marker following administration with the vascular disrupting agent, wherein the biological marker is selected from Serum Amyloid P (SAP), Sex Hormone-Binding Globulin (SHBG), Myoglobin, Matrix Metalloproteinase 9 (MMP-9), and/or Stem Cell Factor (SCF), and wherein a level of a biological marker prior to administration with the vascular disrupting agent that is different to the level of the biological marker following administration with the vascular disrupting agent is indicative of the patient responding to treatment with the vascular disrupting agent.

In a second aspect there is provided a method of treating cancer in a patient, the method comprising performing the method for predicting a response to treatment as described herein and further administering the vascular disrupting agent to the patient.

In one embodiment, the response to treatment with the vascular disrupting agent is an increase in progression free survival. In one particular embodiment, the increase in progression free survival is at least 10 days, at least 15 days, at least 20 days, at least 30 days, at least 40 days, or at least 50 days.

In a third aspect there is provided a method of treating cancer in a patient, the method comprising:

(a) identifying a patient having a level of a biological marker prior to administration with a vascular disrupting agent which is different to the level of the biological marker following administration with the vascular disrupting agent, and (b) further administering the vascular disrupting agent to the patient, wherein the biological marker is selected from SAP, SHBG, Myoglobin, MMP-9, and/or SCF.

In a fourth aspect there is provided a method of treating cancer in a patient, the method comprising administering a vascular disrupting agent to the patient, wherein the patient has a level of a biological marker prior to administration with the vascular disrupting agent which is different to the level of the biological marker following administration with the vascular disrupting agent, and wherein the biological marker is selected from SAP, SHBG, Myoglobin, MMP-9, and/or SCF.

In a fifth aspect there is provided a method of selecting a cancer patient for treatment with a vascular disrupting agent, the method comprising performing the method for predicting response to treatment as described herein and selecting a patient having a level of a biological marker prior to administration with the vascular disrupting agent which is different to the level of the biological marker following administration with the vascular disrupting agent, wherein the biological marker is selected from SAP, SHBG, Myoglobin, MMP-9, and/or SCF.

In one embodiment of first to fifth aspects, the method comprises determining the level of the biological marker in a sample obtained from the patient.

While any suitable sample may be used, in one embodiment the sample is tumor, blood, serum or plasma.

The skilled person will appreciate that determining the level of a biological marker in a patient sample may comprise determining the level of a biological marker nucleic acid or a biological marker polypeptide. Thus, in one embodiment, the level of the biological marker is determined by measuring the level of biological marker polypeptide.

In one embodiment, the method comprises determining the level of the biological marker in a sample obtained from the patient prior to administration with the vascular disrupting agent and/or in a sample obtained from the patient following administration with the vascular disrupting agent.

In one embodiment, the biological marker is selected from SAP, SHBG, and/or Myoglobin and the level of the biological marker is lower following administration with the vascular disrupting agent when compared to the level of the biological marker prior to administration with the vascular disrupting agent.

In one embodiment, the biological marker is SAP and the ratio of the post administration level to pre-administration level of SAP is ≤1. In one particular embodiment, the ratio of the post administration level to pre-administration level of SAP is ≤0.95.

In another embodiment, the biological marker is SHBG and the ratio of the post administration level to pre-administration level of SHBG is ≤1. In one particular embodiment, the ratio of the post administration level to pre-administration level of SHBG is ≤0.92.

In yet another embodiment, the biological marker is Myoglobin and the ratio of the post administration level to pre-administration level of Myoglobin is ≤1. In one particular embodiment, the ratio of the post administration level to pre-administration level of Myoglobin is ≤0.93.

In another embodiment, the biological marker is selected from MMP-9 and/or SCF and the level of the biological marker is higher following administration with the vascular disrupting agent when compared to the level of the biological marker prior to administration with the vascular disrupting agent.

In one embodiment, the biological marker is MMP-9 and the ratio of the post administration level to pre-administration level of MMP-9 is ≥1. In one particular embodiment, the ratio of the post administration level to pre-administration level of MMP-9 is ≥1.06.

In another embodiment, the biological marker is SCF and the ratio of the post administration level to pre-administration level of SCF is ≥1.

In yet another embodiment, the vascular disrupting agent is a tubulin polymerisation inhibitor.

In one particular embodiment, the tubulin polymerisation inhibitor is selected from ABT-751, MPC-6827, AEZS-112, CYT997, MN-029, EPC2407, ZIO-301, vinflunine, vinblastine, vincristine, CA4, Oxi4503, AVE8062, eribulin mesylate, dolastatin, tasidotin, 2-methoxyestradiol, E7974 and/or NPI-2358.

In another embodiment, the tubulin polymerisation inhibitor is a compound of formula (I) or a salt, solvate or prodrug thereof

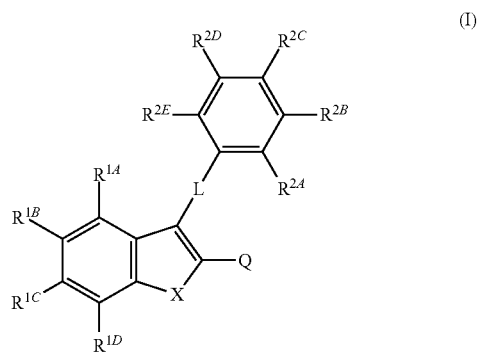

wherein;

X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, SO$_2$, Se, SeO, SeO$_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

In one embodiment, the compound of formula (I) is a prodrug selected from an ester, an acetate, a phosphate ester or an amide prodrug. In another embodiment, the compound of formula (I) is a phosphate prodrug. In a particular embodiment, $R^{1D}$ is hydroxy and the prodrug is a phosphate ester of the hydroxy group. Preferably, the phosphate ester is a disodium phosphate ester.

In another embodiment, the tubulin polymerisation inhibitor is a compound of formula (III) or a salt, solvate or prodrug thereof

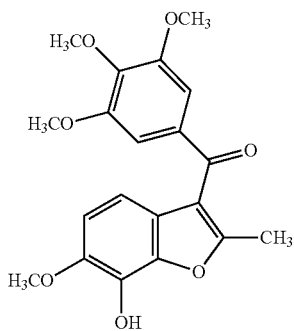 [SMILES: COc1cc(C(=O)c2c(C)oc3c(O)c(OC)ccc23)cc(OC)c1OC]

In yet another embodiment, the tubulin polymerisation inhibitor is selected from 2-methyl-7-hydroxy-3-(3,4,5-trimethoxybenzoyl)-6-methoxybenzofuran (BNC105) and disodium [6-methoxy-2-methyl-3-(3,4,5-trimethoxybenzoyl)-1-benzofuran-7-yl]phosphate (BNC105P).

While the patient may be any patient who would benefit from treatment with a vascular disrupting agent, in one embodiment, the patient is a renal cancer patient.

In one embodiment of the second to fifth aspects, the method further comprises administering a further therapeutic agent and/or tumor irradiation to the patient.

In one embodiment, the further therapeutic agent is selected from a chemotherapeutic, an antibody and/or an immunotherapeutic. In one particular embodiment, the therapeutic agent is selected from an mTOR inhibitor, tyrosine kinase inhibitor and/or a VEGF inhibitor.

In a sixth aspect there is provided a kit for monitoring the response of a patient to treatment with a vascular disrupting agent, the kit comprising agents for detecting and/or quantifying biological markers selected from SAP, SHBG, Myoglobin, MMP-9, and/or SCF.

In one embodiment of the sixth aspect, the agents for detecting and/or quantifying biological markers are attached to a solid support.

In a seventh aspect there is provided a device for directing treatment of a patient with a vascular disrupting agent, the device comprises agents for quantifying biological markers selected from SAP, SHBG, Myoglobin, MMP-9, and/or SCF.

In one embodiment, the device comprises a tube, dipstick, array or multi-well plate.

In one embodiment of the sixth or seventh aspect, the agents for detecting and/or quantifying biological markers are detectably labelled.

In another embodiment, the agents bind the biological markers.

In yet another embodiment, the agents are antibodies.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

KEY TO THE SEQUENCE LISTING

Figure 1:
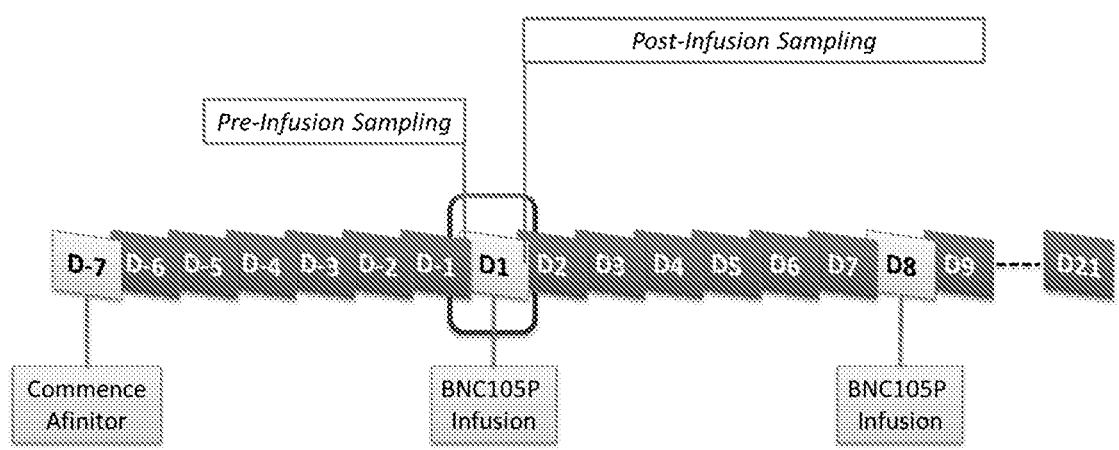
FIG. 1. Dosing schedule for administration of Afinitor (everolimus) and BNC105P. Samples for the testing of biomarkers were taken at Day 1 (pre and post infusion with BNC105P) and at Day 8 (pre and post infusion with BNC105P).
Figure 2A:
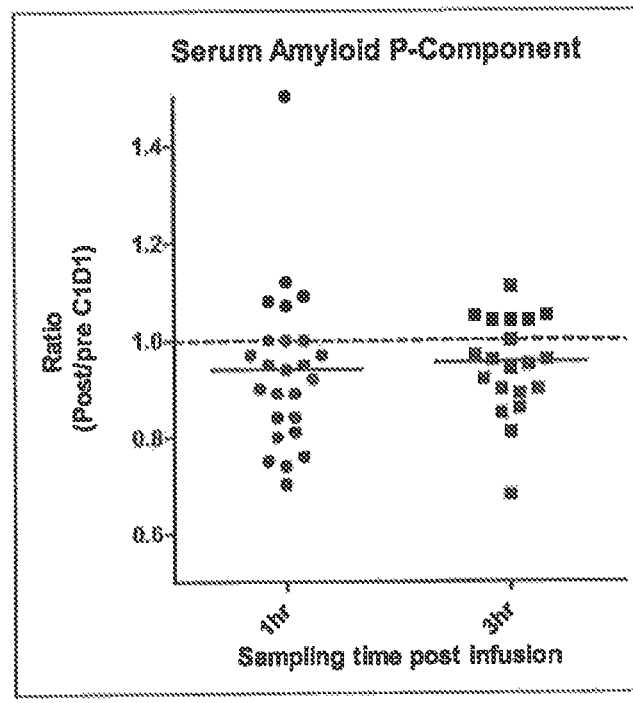
FIG. 2A: Ratio of SAP biomarker level post infusion versus pre infusion with BNC105P.
Figure 2B:
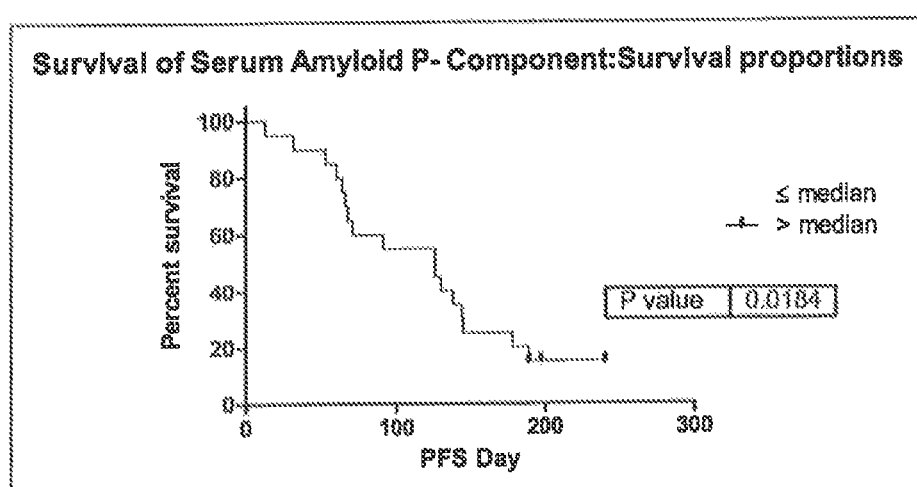
FIG. 2B: Survival proportions separated into two groups based on the median of the ration of [Biomarker]$_{POST\ BNC105P}$/[Biomarker]$_{BASELINE}$.
Figure 3A:
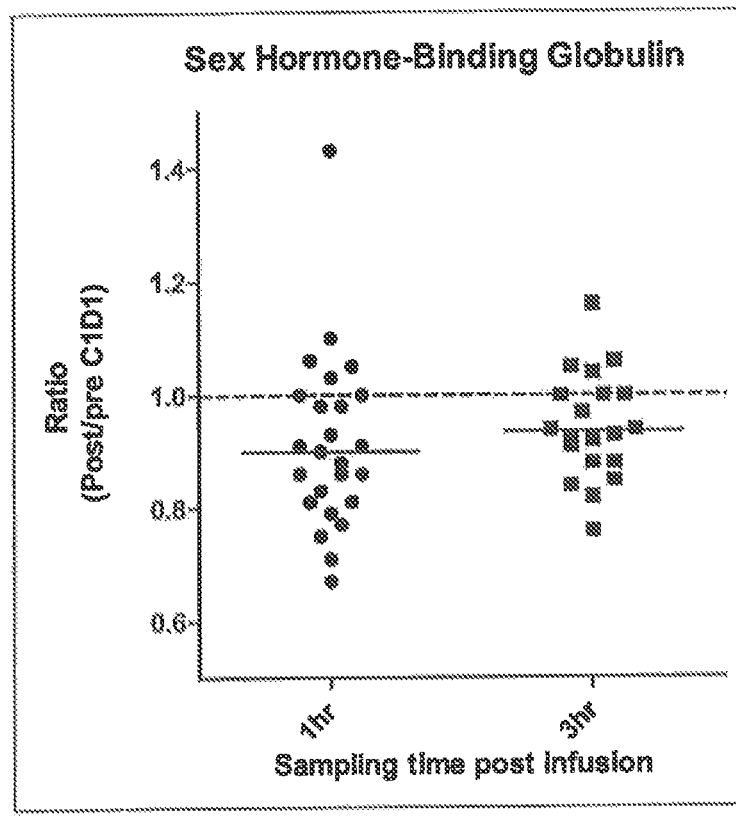
FIG. 3A: Ratio of SHBG biomarker level post infusion versus pre infusion with BNC105P.
Figure 3B:
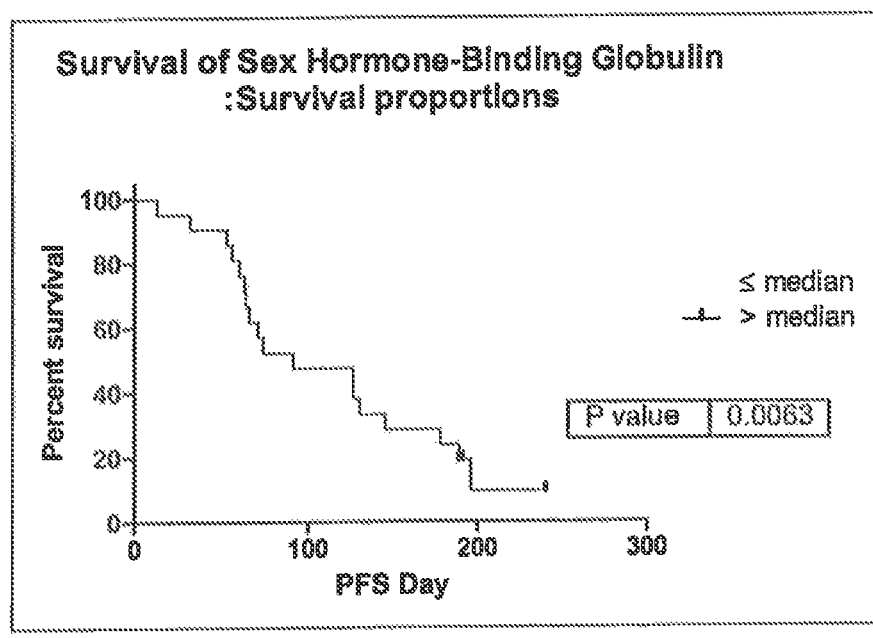
FIG. 3B: Survival proportions separated into two groups based on the median of the ration of [Biomarker]$_{POST\ BNC105P}$/[Biomarker]$_{BASELINE}$.
Figure 4A:
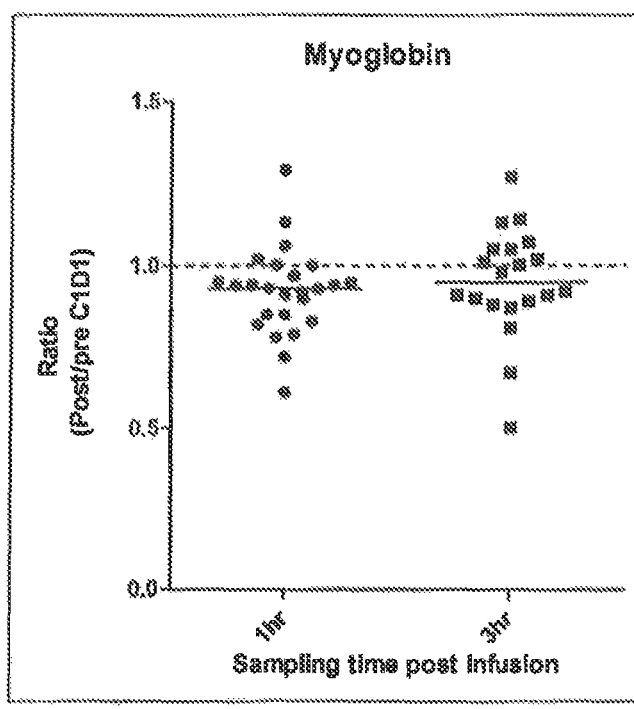
FIG. 4A: Ratio of Myoglobin biomarker level post infusion versus pre infusion with BNC105P.
Figure 4B:
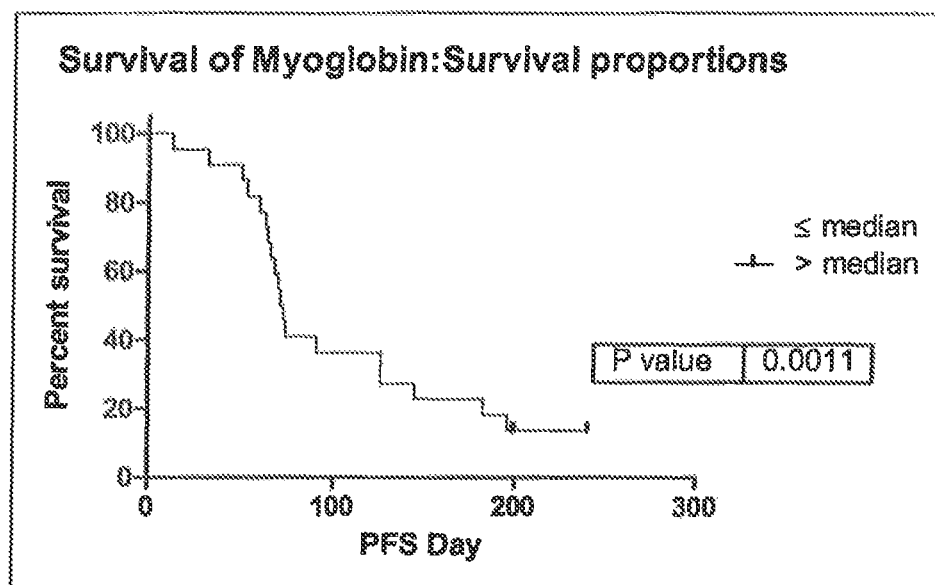
FIG. 4B: Survival proportions separated into two groups based on the median of the ration of $[\text{Biomarker}]_{POST\ BNC105P}/[\text{Biomarker}]_{BASELINE}$.
Figure 5A:
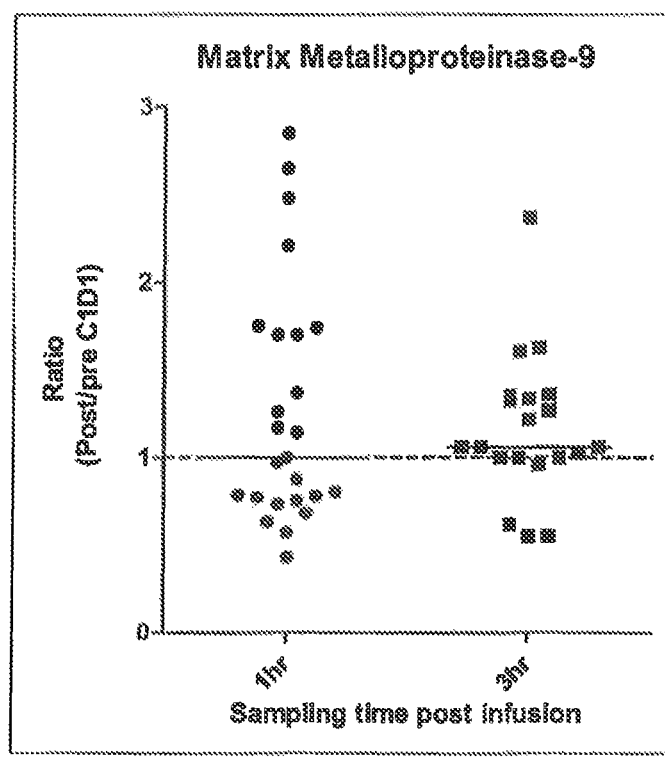
FIG. 5A: Ratio of MMP-9 biomarker level post infusion versus pre infusion with BNC105P.
Figure 5B:
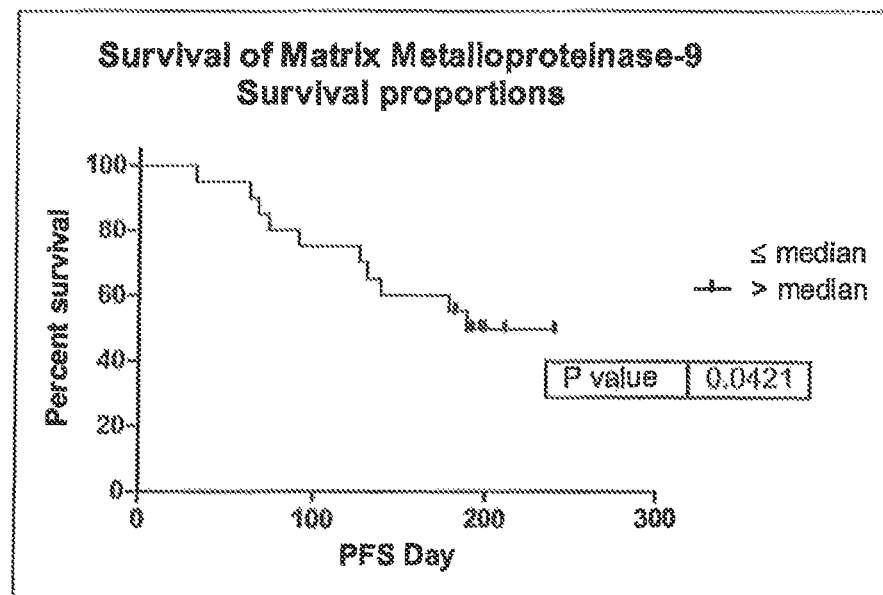
FIG. 5B: Survival proportions separated into two groups based on the median of the ration of $[\text{Biomarker}]_{POST\ BNC105P}/[\text{Biomarker}]_{BASELINE}$.
Figure 6A:
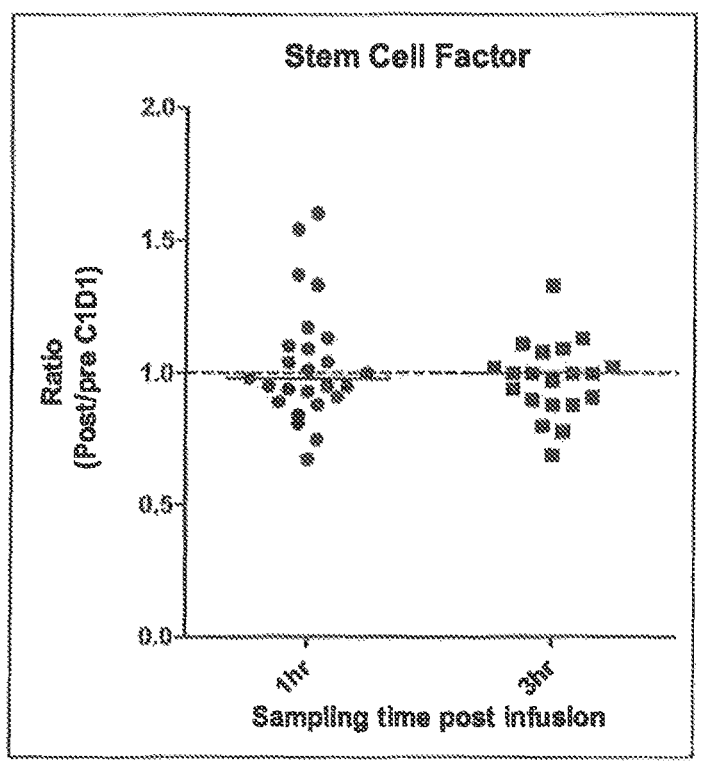
FIG. 6A: Ratio of SCF biomarker level post infusion versus pre infusion with BNC105P.
Figure 6B:
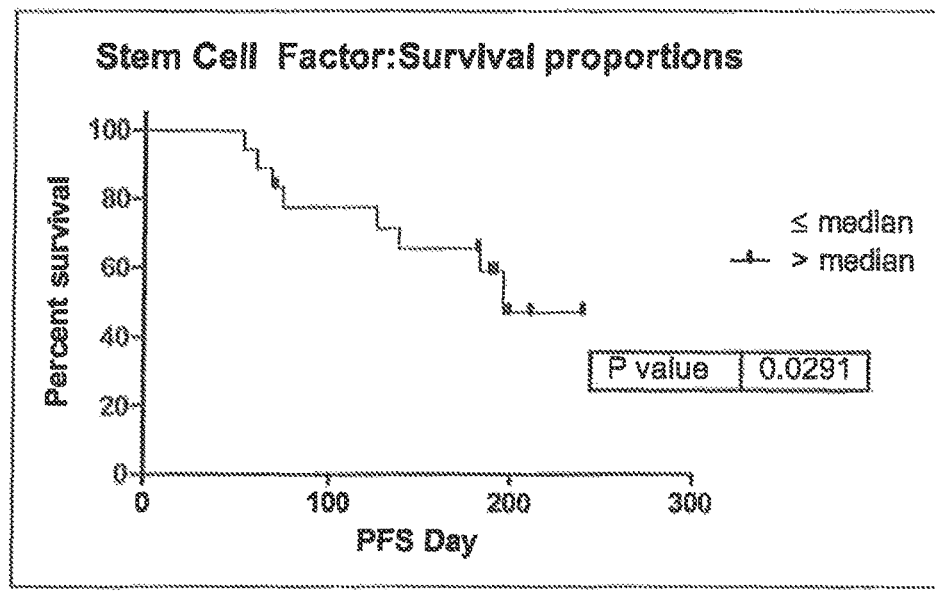
FIG. 6B: Survival proportions separated into two groups based on the median of the ration of $[\text{Biomarker}]_{POST\ BNC105P}/[\text{Biomarker}]_{BASELINE}$.

SEQ ID NO:1—Example of amino acid sequence of Serum Amyloid P-Component (SAP)
SEQ ID NO:2—Example of amino acid sequence of Sex Hormone-Binding Globulin (SHBG)
SEQ ID NO:3—Example of amino acid sequence of Myoglobin (MB)
SEQ ID NO:4—Example of amino acid sequence of Matrix Metalloproteinase-9 (MMP-9)
SEQ ID NO:5—Example of amino acid sequence of Stem Cell Factor (SCF)

DETAILED DESCRIPTION

General Techniques and Definitions

Unless specifically defined otherwise, all technical and scientific terms used herein shall be taken to have the same meaning as commonly understood by one of ordinary skill in the art (e.g., in molecular genetics, biochemistry, chemistry and immunology).

Unless otherwise indicated, the molecular genetics, biochemistry, and immunological techniques utilized in the present invention are standard procedures, well known to those skilled in the art. Such techniques are described and explained throughout the literature in sources such as, J, Perbal, A Practical Guide to Molecular Cloning, John Wiley and Sons (1984), J. Sambrook and Russell., Molecular Cloning: A Laboratory Manual, 3$^{rd}$ edn, Cold Spring Harbour Laboratory Press (2001), R. Scopes, Protein Purification—Principals and Practice, 3$^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10% of the designated value.

As used herein, the terms "treating", "treat" or "treatment" include administering a vascular disrupting agent to a patient for the purpose of preventing or delaying disease progression and/or to increase the duration of progression free survival as compared to a patient who has not been administered the vascular disrupting agent.

As used herein, the terms "response", "responding", "response to treatment" or "responding to treatment" refer to a patient having a reduction in one or more symptoms or signs of disease and/or a delay or prevention of disease progression, and/or a longer period of disease free progression during and/or following treatment with a vascular disrupting agent when compared to a patient that has not been treated with the vascular disrupting agent, and/or to a patient not having a change in the level of a biological marker pre-versus post-administration with the vascular disrupting agent as described herein.

"Administering" as used herein is to be construed broadly and includes administering a composition or therapeutic agent as described herein to a subject or patient as well as providing the composition or therapeutic agent to a cell, such as, for example, by the provision of a prodrug to a patient.

A "sample" may be of any suitable type and may refer, e.g., to a material in which the presence or level of biological markers can be detected. Preferably, the sample is obtained from the subject so that the detection of the presence and/or level of biomarkers may be performed in vitro. Alternatively, the presence and/or level of biomarkers can be detected in vivo. The sample can be used as obtained directly from the source or following at least one step of (partial) purification. The sample can be prepared in any convenient medium which does not interfere with the method of the invention. Typically, the sample is an aqueous solution, biological fluid, cells or tissue, such as tumor tissue. Preferably, the sample is blood, plasma, or serum. Pre-treatment may involve, for example, preparing plasma from blood, diluting viscous fluids, and the like. Methods of treatment can involve filtration, distillation, separation, concentration, inactivation of interfering components, and the addition of reagents. The selection and pre-treatment of biological samples prior to testing is well known in the art and need not be described further.

Biomarkers Predictive of Patient Response to Treatment

The present inventors have analysed the level of biological markers in patients prior to and following infusion of a vascular disrupting agent. This led to the finding that patients having a level of a biological marker prior to administration with the vascular disrupting agent which is different to the level of the biological marker following administration with the vascular disrupting agent have an increased likelihood of responding to treatment with a vascular disrupting agent, wherein the biological marker is selected from Serum Amyloid P-Component, Sex Hormone-Binding Globulin, Myoglobin, Matrix Metalloproteinase-9, and/or Stem Cell Factor.

Serum Amyloid P-Component (SAP)

Serum Amyloid P-Component (SAP) is the identical serum form of amyloid P component (AP), a 25 kDa pentameric protein first identified as the pentagonal constituent of in vivo pathological deposits called "amyloid". SAP is a member of the pentraxins family, characterised by calcium dependent ligand binding and distinctive flattened 3-jellyroll structure similar to that of the legume lectins. The cDNA for the P component of human serum amyloid was isolated and the complete sequence of the precursor determined in 1985 (Mantzouranis et al., 1985). As known in the art, alternative symbols for Serum Amyloid P-Component include Serum Amyloid P, SAP, Short Pentraxin 2, and PTX2 (OMIM Reference 104770). The HUGO Gene Nomenclature Committee (HGNC) approved symbol is APCS. One non-limiting example of the amino acid sequence of SAP is provided as SEQ ID NO: 1. The skilled person will appreciate that this sequence is merely representative and that some variation in the sequence of SAP exists naturally in the human population.

Sex Hormone-Binding Globulin (SHBG)

Sex Hormone-Binding Globulin is known by the alternative titles: Androgen-Binding Protein, ABP, Testosterone-Binding Beta-Globulin, and TEBG (OMIM Reference 182205). The HGNC approved symbol is SHBG. The SBHG gene was characterised by Gershagen et al. in 1989. One non-limiting example of the amino acid sequence of SHBG is provided as SEQ ID NO:2. The skilled person will appreciate that this sequence is merely representative and that some variation in the sequence of SHBG exists naturally in the human population.

Myoglobin (MB)

Myoglobin (MB) is an iron- and oxygen-binding protein found in the muscle tissue of vertebrates in general and in almost all mammals. It is related to hemoglobin, which is the iron- and oxygen-binding protein in blood, specifically in the red blood cells. Another known symbol for Myoglobin is MB, which is also the HGNC approved symbol (OMIM Reference 160000). One non-limiting example of the amino acid sequence of MB is provided as SEQ ID NO:3. The skilled person will appreciate that this sequence is merely representative and that some variation in the sequence of MB exists naturally in the human population.

Matrix Metalloproteinase-9 (MMP-9)

Matrix metalloproteinases are zinc-dependent endopeptidases and belong to a larger family of proteases known as the metzincin superfamily. MMP-9 catalyses the cleavage of gelatin types I and V and collagen types IV and V. Alternative titles and symbols for MMP-9 include Collagenase Type IV-B, CLG4B, 92-kD Collagenase Type IV, Collagenase Type V, 92-kD Gelatinase, Gelatinase B, GELB (OMIM Reference 120361). The HGNC approved symbol is MMP9. One non-limiting example of the amino acid sequence of MMP-9 is provided as SEQ ID NO:4. The skilled person will appreciate that this sequence is merely representative and that some variation in the sequence of MMP-9 exists naturally in the human population.

Stem Cell Factor (SCF)

Stem cell factor (SCF) is a hematopoietic growth factor and ligand for the KIT tyrosine kinase receptor. Alternative names for SCF include Kit Ligand, KITLG, KL, KITL, Mast Cell Growth Factor, MGF, MGF Stem Cell Factor, Steel Factor, and SF. The HGNC approved Gene Symbol is KITLG (OMIM Reference 184745). One non-limiting example of the amino acid sequence of SCF is provided as SEQ ID NO:5. The skilled person will appreciate that this sequence is merely representative and that some variation in the sequence of SCF exists naturally in the human population.

Personalised Medicine

The methods of the present invention can be used to identify those patients with an increased likelihood of responding to treatment with a vascular disrupting agent. Thus, the terms "prediction" and "predicting" as used herein refer to the likelihood that a patient will respond favorably to a vascular disrupting agent. In one embodiment, the prediction relates to whether and/or the probability that a patient will have an increased period of disease free progression following administration with a vascular disrupting agent. The predictive methods of the invention can be used to make treatment decisions by choosing the most appropriate treatment modalities for any particular patient, for example by directing a particular course of treatment, or adjusting doses or directing that a treatment be discontinued. For example, the method of the invention may be used to determine i) whether treatment with a vascular disrupting agent in a patient should be commenced following a first test infusion of the agent; ii) whether an already commenced treatment with a vascular disrupting agent should be continued in view of the patient having an increased likelihood of responding to the agent; or iii) whether an already commenced treatment with a vascular disrupting agent should be ceased in view of the patient having a reduced likelihood of responding to the agent.

In one embodiment, the patient is an individual likely to benefit from treatment with a vascular disrupting agent. By way of non-limiting examples, patients likely to benefit from treatment with a vascular disrupting agent include patients with cancer, age related macular degeneration and endometriosis.

In certain embodiments, the patient that is selected for treatment according to the method of the invention is a cancer patient, in particular a cancer patient with a solid tumor. A solid tumor can be malignant or benign. Examples of solid tumors that can be treated according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, ovarian cancer, fallopian tube cancer, primary carcinoma of the peritoneum, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cancer, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Biomarker Screening

Any suitable method known to one of skill in the art for detecting the level of biological markers in a patient may be used in the present invention. Thus, the methods of the invention may involve a degree of quantification to determine levels of biological markers (also referred to as "biomarkers") in patient samples. Such quantification is readily provided by the inclusion of appropriate control samples or by comparison to reference data.

In one embodiment, internal controls are included in the methods of the present invention. In one embodiment, a preferred internal control is one or more samples taken from one or more individuals who have not been administered with a vascular disrupting agent, and/or one or more samples taken from a patient following administration with a vascular disrupting agent.

As will be known to those skilled in the art, when internal controls are not included in each assay conducted, the control may be derived from reference data (i.e. an established data set). Data pertaining to the control subjects may be selected from the group consisting of:

1. a data set comprising measurements of the level of biomarkers for a typical population of subjects prior to and/or following administration with a vascular disrupting agent;

2. a data set comprising measurements of the level of biomarkers for the subject being tested wherein said measurements have been made previously, such as, for example, prior to the administration of a vascular disrupting agent or prior to the commencement of treatment;

3. a data set comprising measurements of level of biomarkers for a healthy individual or a population of healthy individuals; and 4. a data set comprising measurements of the level of biomarkers for a normal individual or a population of normal individuals.

Compounds that bind a biological marker when used according the invention may be linked to a reagent such as a detectable label to allow easy detection of binding events in vitro or in vivo. Suitable labels include radioisotopes, dye markers or other imaging reagents for detection and/or localisation of target molecules. Compounds linked to a detectable label can be used with suitable in vivo imaging technologies such as, for example, radiology, fluoroscopy, nuclear magnetic resonance imaging (MRI), CAT-scanning, positron emission tomography (PET), computerized tomography etc.

In one embodiment, the level of a biological marker polypeptide is determined in a patient sample. For example, the method may comprise contacting a biological sample derived from the patient with a compound capable of binding to a biomarker polypeptide, and detecting the formation of complex between the compound and the biomarker polypeptide. The terms "biological marker polypeptide" or "biomarker polypeptide" as used herein include fragments of biomarker polypeptides, including for example, immunogenic fragments and epitopes of the biomarker polypeptide.

In one embodiment, the compound that is used to detect or bind to the biological marker is an antibody. The term "antibody" as used herein includes intact molecules as well as molecules comprising or consisting of fragments thereof, such as, for example Fab, F(ab')2, Fv and scFv, as well as engineered variants including diabodies, triabodies, minibodies and single-domain antibodies which are capable of binding an epitopic determinant. Thus, antibodies may exist as intact immunoglobulins, or as modifications in a variety of forms.

Protein detection systems contemplated herein include any known assay for detecting proteins in a biological sample isolated from a human subject, such as, for example, SDS/PAGE, isoelectric focussing, 2-dimensional gel electrophoresis comprising SDS/PAGE and isoelectric focussing, an immunoassay, flow cytometry e.g. fluorescence-activated cell sorting (FACS), a detection based system using an antibody or non-antibody compound, such as, for example, a small molecule (e.g. a chemical compound, agonist, antagonist, allosteric modulator, competitive inhibitor, or non-competitive inhibitor, of the protein). In accordance with these embodiments, the antibody or small molecule may be used in any standard solid phase or solution phase assay format amenable to the detection of proteins. Optical or fluorescent detection, such as, for example, using mass spectrometry, MALDI-TOF, biosensor technology, evanescent fiber optics, or fluorescence resonance energy transfer, is clearly encompassed by the present invention.

Assay systems suitable for use in high throughput screening of mass samples, e.g. a high throughput spectroscopy resonance method (e.g. MALDI-TOF, electrospray MS or nano-electrospray MS), are also contemplated. Another suitable protein detection technique involves the use of Multiple Reaction Monitoring (MRM) in LC-MS (LC/MRM-MS).

Immunoassay formats are also suitable, for example, such as those selected from the group consisting of, an immunoblot, a Western blot, a dot blot, an enzyme linked immunosorbent assay (ELISA), radioimmunoassay (RIA), enzyme immunoassay. Modified immunoassays utilizing fluorescence resonance energy transfer (FRET), isotope-coded affinity tags (ICAT), matrix-assisted laser desorption/ionization time of flight (MALDI-TOF), electrospray ionization (ESI), biosensor technology, evanescent fiber-optics technology or protein chip technology are also useful.

In another embodiment, a nucleic acid detection technique is used. Any suitable technique that allows for the qualitative and/or quantitative assessment of the level of a biomarker polynucleotide in a sample as known in the art may be used. The terms "nucleic acid molecule" or "polynucleotide" as used herein refer to an oligonucleotide, polynucleotide or any fragment thereof.

Comparison may be made by reference to a standard control, a control level, or reference sample or reference level. For example, levels of a transcribed gene can be determined by Northern blotting, and/or RT-PCR. With the advent of quantitative (real-time) PCR, quantitative analysis of gene expression can be achieved by using appropriate primers for the gene of interest. The nucleic acid may be labelled and hybridised on a gene array, in which case the gene concentration will be directly proportional to the intensity of the radioactive or fluorescent signal generated in the array.

Methods for direct sequencing of nucleotide sequences are well known to those skilled in the art and can be found for example in Ausubel et al., eds., Short Protocols in Molecular Biology, 3rd ed., Wiley, (1995) and Sambrook et al, Molecular Cloning, 3rd ed., Cold Spring Harbor Laboratory Press, (2001). Sequencing can be carried out by any suitable method, for example, dideoxy sequencing, chemical sequencing or variations thereof. Direct sequencing has the advantage of determining variation in any base pair of a particular sequence.

In one embodiment, the direct sequencing is Next-generation high-throughput sequencing. Next-generation sequencing (NGS) technologies include instruments that are capable of sequencing more than $10^{14}$ kilobase-pairs (kbp) of DNA per instrument run. Sequencing typically produces a large number of independent reads, each representing anywhere between 10 to 1000 bases of the nucleic acid. Nucleic acids are generally sequenced redundantly for confidence, with replicates per unit area being referred to as the coverage (i.e., "10× coverage" or "100× coverage"). Next generation sequencing methods are known in the art, and are described, for example, in Metzker (2010).

Thus, the terms "Next-generation sequencing" or "NGS" or "NG sequencing" as used herein refer to any sequencing method that determines the nucleotide sequence of either individual nucleic acid molecules (e.g., in single molecule sequencing) or clonally expanded proxies for individual nucleic acid molecules in a high through-put fashion (e.g., greater than $10^3$, $10^4$, $10^5$ or more molecules are sequenced simultaneously).

Platforms for next-generation sequencing include, but are not limited to, Roche/454's Genome Sequencer (GS) FLX System, Illumina/Solexa's Genome Analyzer (GA), Life/

APG's Support Oligonucleotide Ligation Detection (SOLiD) system, Polonator's G.007 system, Helicos BioSciences' HeliScope Gene Sequencing system, and Pacific Biosciences' PacBio RS system.

Other PCR methods that may be used in carrying out the invention include hybridization based PCR detection systems, TaqMan assay (U.S. Pat. No. 5,962,233) and the molecular beacon assay (U.S. Pat. No. 5,925,517).

The nucleic acid may be separated from the sample for testing. Suitable methods will be known to those of skill in the art. For example, RNA may be isolated from a sample to be analysed using conventional procedures, such as are supplied by QIAGEN technology. This RNA is then reverse-transcribed into DNA using reverse transcriptase and the DNA molecule of interest may then be amplified by PCR techniques using specific primers.

Nucleic acid assays may also be performed directly upon patient samples. Hybridisation or amplification assays, such as, for example, Southern or Northern blot analysis, immunohistochemistry, single-stranded conformational polymorphism analysis (SSCP) and PCR analyses are among techniques that are useful in this respect. If desired, target or probe nucleic acid may be immobilised to a solid support such as a microtitre plate, membrane, polystyrene bead, glass slide or other solid phase.

In one embodiment, the level of a biological marker may be determined using a suitable commercially available test. By way of non-limiting example, the level of a biomarker may be quantitatively measured using the Multi-Analyte Profile (MAP) Technology (Myriad RBM).

The level of the biological marker in a patient sample prior to administration of the vascular disrupting agent may be determined from a sample taken at any time prior to administration of a first dose of the vascular disrupting agent. In one embodiment, the sample is taken within 1 month, or within 1 week, or within 3 days, or within 48 hours, or within 24 hours, or within 3 hours, or within 1 hour prior to the first dose of the vascular disrupting agent.

The level of the biological marker in a patient sample following administration of the vascular disrupting agent may be determined from a sample taken at any time following the administration of the vascular disrupting agent within which the biological marker is likely to maintain an altered level due to administration of the agent. In one embodiment, the sample is taken within 48 hours, or within 24 hours of administration with the vascular disrupting agent. In another embodiment, the sample is taken within 3 hours of administration with the vascular disrupting agent. In another embodiment, the sample is taken within 1 hour of administration with the vascular disrupting agent.

As known in the art, the level of a biological marker may be determined according to the detection technique used. Thus, the level of a biological marker may be, for example, a level of expression, transcription or translation of a polynucleotide, the level of expression of a polypeptide and/or the concentration of a biological marker in a sample. By way of non-limiting example, the level of a biomarker may be determined or inferred by detection of a label, via colorimetric change, alterations in signal intensities, such as by determining the wavelength or strength of a fluorescent signal, by measuring absorbance or optical density, by measuring radioactive signals. In one embodiment, the level of a biomarker is presented as the concentration of the biological marker in a sample obtained from the patient. A concentration of a biological marker may be presented in any suitable unit such as, for example, ng/ml, µg/ml, mg/ml, pg/µl, or µg/l.

Devices and Kits

The present invention further provides devices, such as predictive or diagnostic devices and kits for determining the level of a biological marker in a patient or patient sample prior to and/or following administration with a vascular disrupting agent. Diagnostic/predictive kits based on the biological markers described above can be developed for use in predicting an individual's response to treatment with a vascular disrupting agent. Such test kits can include devices and instructions that a subject can use to obtain a sample, e.g., blood, plasma or serum, in some instances with the aid of a health care provider.

Thus, it will be appreciated that the method of the invention may be used as a "companion diagnostic" to a therapeutic treatment or method in order to validate or direct the use of the therapeutic. Companion diagnostics are increasingly finding utility in the justification of expensive or high risk treatments which only confer benefit to a subset of the population. A companion diagnostic test refers to an in vitro diagnostic device or kit, or an imaging tool, the use of which indicates an increased likelihood of a patient responding to treatment. In-vitro Companion Diagnostic tests measure the expression or presence of a specific biomarker that is linked to a disease condition or therapy.

In one embodiment, the device of the invention, for example a companion diagnostic device, is an array. The term "array" or "microarray", as used herein refers to an ordered arrangement of hybridizable array elements, such as polynucleotide probes (e.g., oligonucleotides), or binding reagents (e.g., antibodies), on a substrate. The substrate can be a solid substrate, such as a glass or silica slide, a bead, a fiber optic binder, or a semi-solid substrate, such as a nitrocellulose membrane. The nucleotide sequences can be DNA, RNA, or any permutations thereof.

In some embodiments, the invention provides compositions and kits comprising primers and primer pairs, which allow the specific amplification of biomarker polynucleotides, and probes that selectively or specifically hybridize to biomarker polynucleotides. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides in a sample and as a means for detecting cell expressing proteins encoded by the polynucleotides. As will be understood by the skilled artisan, a great many different primers and probes may be prepared based on the sequences provided herein and used effectively to amplify, clone and/or determine the presence and/or levels of the biological markers described herein.

In some embodiments, the device or kit comprises reagents for detecting the presence of biological marker polypeptides. Such reagents may be antibodies or other binding molecules that specifically bind to a polypeptide. The antibodies or binding molecules may be labeled with a detectable marker, such as, for example, a radioisotope, a fluorescent compound, a bioluminescent compound, a chemiluminescent compound, a metal chelator, an enzyme, or a particle. Other reagents for performing binding assays, such as ELISA, may be included in the kit.

In some embodiments, the kits comprise reagents for detecting or determining the level of at least two, at least three, at least four, or all of the biological markers described herein. In some embodiments, the kits may further comprise a surface or substrate (such as a microarray) for capture probes for detecting of amplified nucleic acids.

The kits may further comprise a carrier being compartmentalized to receive in close confinement one or more containers such as vials, tubes, and the like, each of the containers comprising one of the separate elements to be used in the method. For example, one of the container means may comprise a probe that is or can be detectably labeled. Such probe may be a polynucleotide or antibody specific for a biomarker. Where the kit utilizes nucleic acid hybridization to detect the target nucleic acid, the kit may also have containers containing nucleotide(s) for amplification of the target nucleic acid sequence and/or a container comprising a reporter, such as a biotin-binding protein, such as avidin or streptavidin, bound to a reporter molecule, such as an enzymatic, florescent, or radioisotope label. In one embodiment, one of the containers may comprise an antibody that is or can be detectably labelled and which binds a biological marker as described herein.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific purpose and may also indicate directions for either in vivo or in vitro use, such as those described above. The kit can further comprise a set of instructions and materials for preparing a tissue or cell sample, for example, blood, plasma or serum, and preparing nucleic acids from the sample.

Vascular Disrupting Agents

Endothelial cells are highly dependent on the tubulin cytoskeleton for their motility, invasion, attachment, alignment and proliferation. Vascular disrupting agents (VDAs) target endothelial cells and pericytes of the already established tumor vasculature. Most VDAs induce changes in endothelial cell shape by disruption of the cytoskeleton and cell-to-cell junctions. This results in increased permeability to proteins and an increased interstitial fluid pressure, which might be sufficient to reduce vessel diameter. Plasma leakage also leads to increased blood viscosity resulting in decreased blood flow and rouleaux formation.

Another factor contributing to the vascular shutdown is the activation of platelets through contact with basement membrane components, which are exposed. All together this cascade of events results in vascular shutdown more selectively in tumor endothelium than normal endothelium. As stated previously, it is suggested that the inhibition of blood flow and the subsequent compromised supply of oxygen and nutrients will induce necrosis of many tumor cells downstream.

Vascular disrupting agents have been divided into two types, small molecule and ligand directed VDAs. Small molecule VDAs are in a more advanced stage of clinical development. Small molecule VDAs include tubulin-binding agents and flavonoids. Tubulin-binding agents are proposed to act at the colchicine-binding site of the β-subunit of endothelial cell tubulin, resulting in depolymerization of microtubules and disorganization of actin and tubulin (e.g. CA4 (combretastatin)).

Disruption of the endothelial cytoskeleton results in cell morphology changes leading to reduction or cessation of blood flow. Tumor-related endothelial cells are much more sensitive to the activity of tubulin-binding agents than normal endothelial cells. ASA404 is a small-molecule flavonoid VDA with activity involving inhibition of pathways that up regulate the nuclear transcription factor NfκB and production of TNF-α and other cytokines.

Thus, in one embodiment, the vascular disrupting agent is a Tubulin Polymerization Inhibitor (TPI). As used herein the term "tubulin polymerisation inhibitor" refers to any and all compounds or molecules which directly interact with tubulin and inhibit tubulin polymerisation and/or depolymerise tubulin and as a consequence interferes with the physiological function of microtubules. Tubulin polymerisation inhibitors (TPIs) are also referred to as microtubule "destabilizing" agents. Such compounds should be contrasted with tubulin interacting compounds like taxanes and epothilones which stabilise tubulin polymers and inhibit tubulin depolymerisation (i.e., microtubule stabilising agents).

Microtubules are filamentous polymers that are key components of the cell cytoskeleton. They are dynamic structures fluctuating between states of polymerisation and depolymerisation. This property enables microtubules to modulate cell shape, adhesion, migration and proliferation. TPIs interfere with microtubule integrity, leading to cytoskeletal changes of the endothelial cells that line the blood vessels of the tumour. As a result, these usually flat cells become more rounded, and lose their cell to cell contact. These events lead to narrowing of tumour blood vessels and ultimately occlusion of blood flow through the vessels. TPIs directly disrupt microtubule polymerisation processes and consequently have the ability to effect cell shape changes and inhibit cell proliferation. These properties are central to the use of TPIs as therapeutics for the treatment of cancer and in the method of the present invention.

TPIs may also be classified based on their specific tubulin binding site. Binding of *vinca* alkaloids to tubulin defines a site that mediates the tubulin destabilization activity seen with these compounds. The "*vinca*" site has been shown to directly bind a number of compounds that effect destabilization of tubulin. Examples of TPI's that bind to the *vinca* site include vinflunine, vinblastine, vincristine, vinorelbine, dolastatin, tasidotin and E7974.

Colchicine binding to tubulin defines an independent binding site that like in the case of the "*vinca*" site causes destabilization of tubulin. Although TPI's binding to the "*vinca*" sites have been successful as anti-cancer chemotherapeutics, "colchicine" site binders have been in comparison neglected, possibly due to the lack of therapeutic margins offered by colchicine. However, more recently a number of "colchicine" site binding agents have been described that have the ability to cause disruption of blood vessels within solid tumors. Many of the "colchicine" site binding agents are based on natural products such as combretastatins (CA4P, OXi-4503, AVE-8062), colchicines (ZD6126) and phenylahistin (NPI-2358) while others are small molecules which bind to the colchicine site (ABT-751, MPC-6827, AEZS-112, CYT-997, MN-029, EPC2407, ZIO-301, 2ME2, ZD6126 and NPI-2358).

TPI compounds are important in the treatment of cancers primarily as a result of their capacity to selectively shut down blood flow through a tumour. Targeting tubulin polymerisation inhibition has been a very well validated anti-cancer approach through the development and now extensive clinical use of chemotherapeutic TPIs.

Examples of TPIs suitable for use in the present invention include ABT-751 (E7010, Abbott), MPC-6827 (Azixa™, Myriad Pharmaceuticals), AEZS-112 (ZEN-012, Eterna Zentaris), CYT997 (Cytopia), MN-029 (Denibulin, MediciNova/Angiogene), EPC2407 (EpiCept), ZIO-301 (Indibulin, Ziopharm Oncology), Vinflunine (Javlor, Pierre Fabre Medicament) as well as other *vinca* alkaloids (e.g., vinblastin, vincristine, and vinorelbine), combretastatins (CA4 (Zybrestat™, OXiGENE), Oxi4503 (OXiGENE), and AVE8062 (AC7700, Sanofi Aventis)), Eribulin Mesylate (E7389, Eisai), Dolastatin 10 (NCI), Tasidotin (synthadotin, Genzyme), 2-methoxyestradiol (2ME2 or Panzem®, EntreMed), E7974 (Eisai), and NPI-2358 (Nereus Pharmaceuticals). Examples of TPI structures are provided in Table 1.

TABLE 1
Examples of TPI structures
ABT-751 (E7010, Abbott)
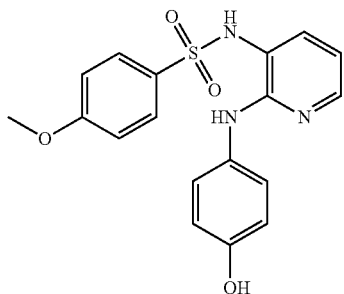
Vinflunine
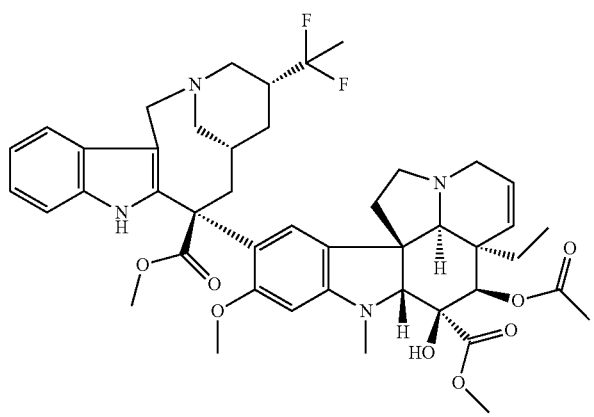
MPC-6827 (Azixa™, Myriad Pharmaceuticals)
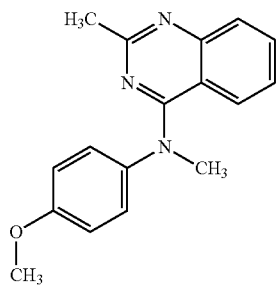
Vinblastin
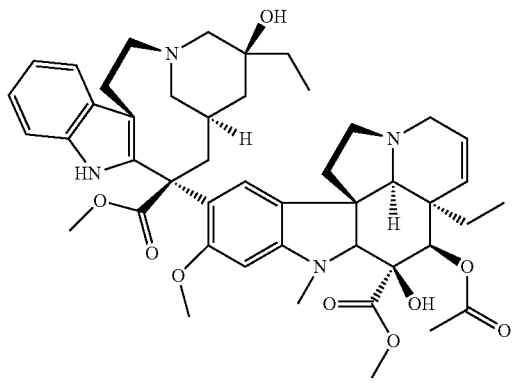

TABLE 1-continued
Examples of TPI structures
AEZS-112 (ZEN-012, Eterna Zentaris)
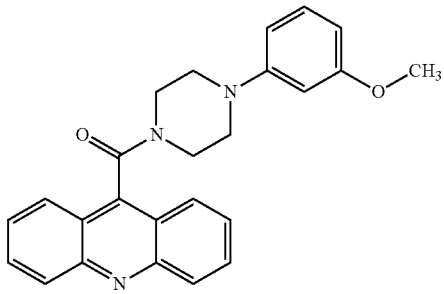
Vincristine
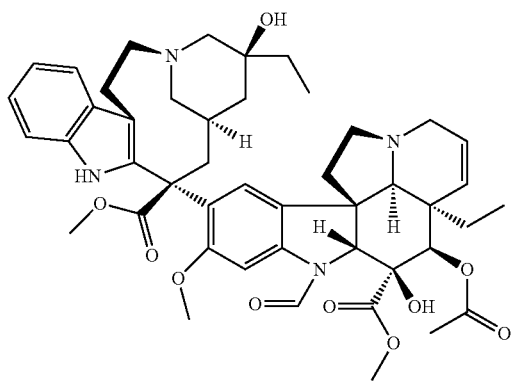
CYT997 (Gilead)
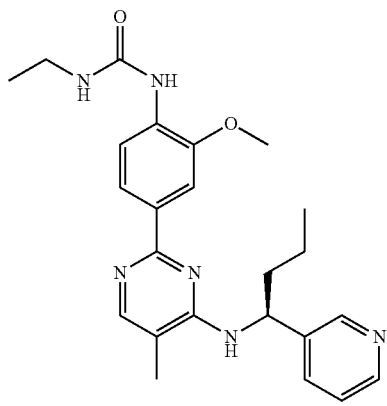
Vinorelbine
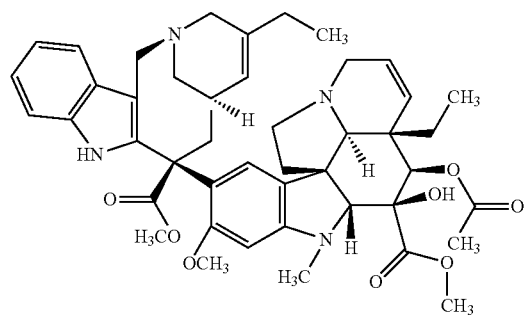

TABLE 1-continued
Examples of TPI structures
MN-029 (Denibulin, MediciNova/Angiogene)
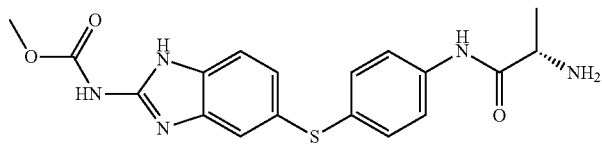
Dolastatin 10 (NCI)
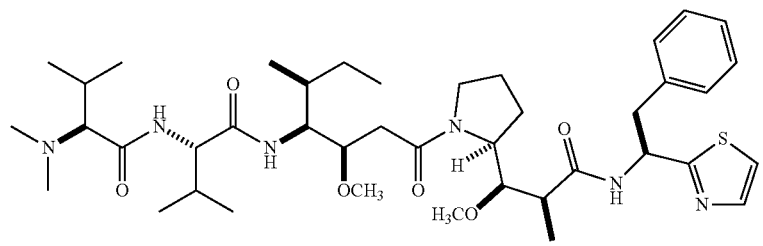
EPC2407 (EpiCept)
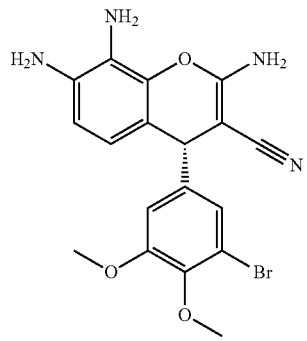
Tasidotin (synthadotin, Genzyme)
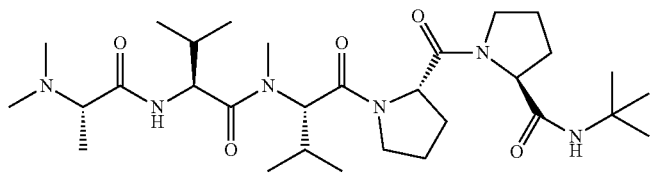
ZIO-301 (Indibulin, Ziopharm Oncology)
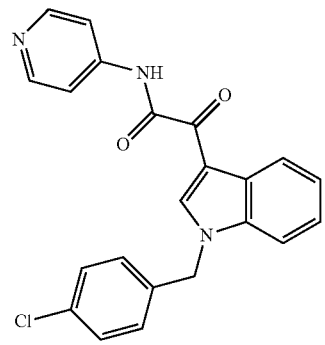

TABLE 1-continued
Examples of TPI structures
E7974 (Eisai)
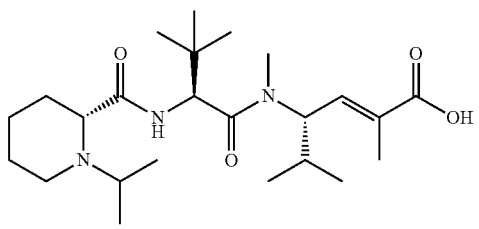
CA4 (Zybrestat™, OXiGENE)
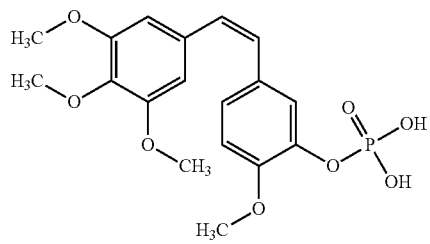
Oxi4503 (OXiGENE)
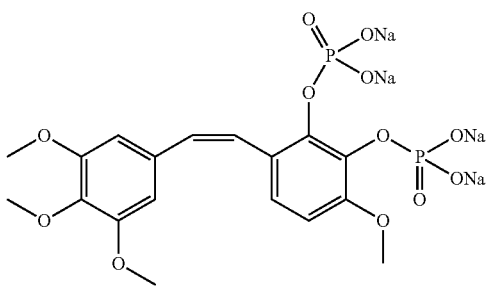
AVE8062 (AC7700, Sanofi Aventis)
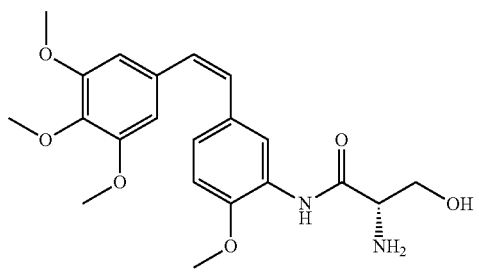

TABLE 1-continued

Examples of TPI structures

Eribulin Mesylate (E7389, Eisai)

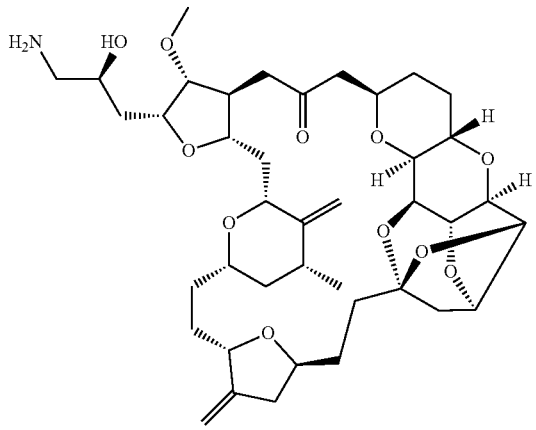

2-methoxyestradiol (2ME2 or Panzem®, EntreMed)

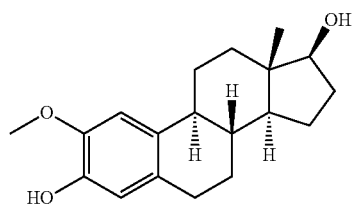

In an embodiment the TPI is selected from a compound of formula (I) or salts, solvates or prodrugs thereof

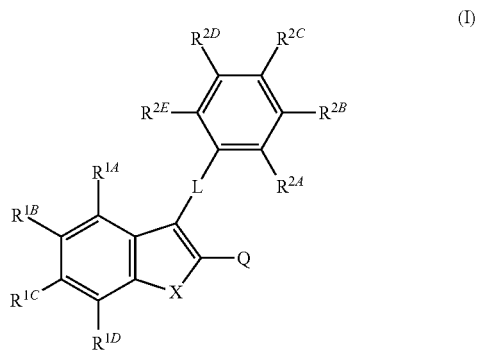

(I)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In some embodiments X is selected from

O,

S,

SO, $SO_2$,

Se,

SeO, $SeO_2$ or

NR where R is selected from

H,

O, optionally substituted acyl selected from H—C(O)—, $C_1$-$C_{10}$ alkyl-C(O)— (preferably $C_1$-$C_6$ alkyl, more preferably $C_1$-$C_3$ alkyl), $C_4$-$C_8$ cycloalkyl-C(O)—, $C_6$-$C_{14}$ aryl-C(O)—, heteroaryl-C(O)— having from 2 to 10 carbon atoms and 1 to 4 heteroatoms selected from oxygen, nitrogen, selenium, and sulfur (including oxides of sulfur, selenium and nitrogen) within the ring or heterocyclyl-C(O)— having from 1 to 8 carbon atoms and from 1 to 4 heteroatoms selected from nitrogen, sulfur, oxygen, selenium or phosphorous within the ring. Examples of suitable acyl groups include formyl acetyl, propionyl, benzoyl (optionally substituted with methyl, methoxy, halogen, nitro, trifluoromethyl or cyano);

optionally substituted monovalent $C_2$-$C_{10}$ alkenyl group which may be straight chained or branched (preferably $C_2$-$C_6$ alkenyl) having at least 1 or from 1-2 carbon to carbon double bonds. Examples of suitable optionally substituted alkenyl groups include, ethenyl, n-propenyl, iso-propenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted $C_1$-$C_{10}$ alkyl (preferably $C_1$-$C_6$ alkyl, more preferably $C_1$-$C_3$ alkyl). Examples of suitable alkyl groups include methyl, ethyl, n-propyl, iso-propyl, n-butyl, iso-butyl, n-hexyl, 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

optionally substituted $C_6$-$C_{14}$ aryl;

optionally substituted $C_4$-$C_8$ cycloalkenyl;

optionally substituted $C_3$-$C_8$ cycloalkyl;

optionally substituted heteroaryl having from 2 to 10 carbon atoms and 1 to 4 heteroatoms selected from oxygen, nitrogen, selenium, and sulfur (including oxides of sulfur, selenium and nitrogen) within the ring;

optionally substituted heterocyclyl having from 1 to 8 carbon atoms and from 1 to 4 heteroatoms selected from nitrogen, sulfur, oxygen, selenium or phosphorous within the ring; and optionally substituted sulfonyl selected from H—S(O)$_2$—, $C_1$-$C_{10}$ alkyl-S(O)$_2$— (preferably $C_1$-$C_6$ alkyl, more preferably $C_1$-$C_3$ alkyl), $C_3$-$C_8$ cycloalkyl-S(O)$_2$—, $C_6$-$C_{14}$ aryl-S(O)$_2$—, heteroaryl-S(O)$_2$— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$— where the heterocyclyl group has from 1 to 8 carbon atoms and from 1 to 4 heteroatoms selected from nitrogen, sulfur, oxygen, selenium or phosphorous within the ring. Examples of sulfonyl groups include methylsulfonyl, ethylsulfonyl, benzenesulfonyl (optionally substituted with methyl, methoxy, halogen, nitro, trifluoromethane or cyano), methoxycarbo, trifluoromethane;

In some embodiments $R^{1A}$-$R^{1B}$ and $R^{2A}$-$R^{2E}$ are independently selected from the following groups:

hydrogen;

$C_1$-$C_{10}$ alkyl, preferably $C_1$-$C_6$ alkyl, more preferably $C_1$-$C_3$ alkyl. Examples of suitable alkyl groups include methyl, ethyl, n-propyl, iso-propyl, n-butyl, iso-butyl and n-hexyl;

substituted $C_1$-$C_{10}$ alkyl group, preferably $C_1$-$C_6$ alkyl, more preferably $C_1$-$C_3$ alkyl. Examples of substituted alkyl groups include 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

optionally substituted acyl group selected from H—C(O)—, $C_1$-$C_{10}$ alkyl-C(O)— (preferably $C_1$-$C_6$ alkyl, more preferably $C_1$-$C_3$ alkyl), $C_3$-$C_8$ cycloalkyl-C(O)—, $C_6$-$C_{14}$ aryl-C(O)—, heteroaryl-C(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring) and heterocyclyl-C(O)— where the heterocyclyl group has from 1 to 8 carbon atoms and from 1 to 4 heteroatoms selected from nitrogen, sulfur, oxygen, selenium or phosphorous within the ring). Examples of acyl groups include formyl acetyl, propionyl, benzoyl (optionally substituted with methyl, methoxy, halogen, nitro, trifluoromethyl or cyano);

optionally substituted $C_1$-$C_{10}$ alkoxy group, preferably $C_1$-$C_6$ alkoxy, more preferably $C_1$-$C_3$ alkoxy. Examples of suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy; optionally substituted oxyacyl group selected from HOC(O)—, $C_1$-$C_{10}$ alkyl-OC(O)— (preferably preferably $C_1$-$C_6$ alkyl, more preferably $C_1$-$C_3$ alkyl), $C_3$-$C_8$ cycloalkyl-OC(O)—, $C_6$-$C_{14}$ aryl-OC(O)—, heteroaryl-OC(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-OC(O)— where the heterocyclyl group has from 1 to 8 carbon atoms and from 1 to 4 heteroatoms selected from nitrogen, sulfur, oxygen, selenium or phosphorous within the ring. Examples of oxyacyl groups include methoxycarbonyl, ethoxycarbonyl, propoxycarbonyl, butyloxycarbonyl, isobutyloxycarbonyl;

optionally substituted acyloxy group selected from —OC(O)—($C_1$-$C_{10}$ alkyl) (preferably $C_1$-$C_6$ alkyl, more preferably $C_1$-$C_3$ alkyl), —OC(O)—($C_6$-$C_{14}$ aryl), —C(O)O-heteroaryl where the heteroaryl group has from 2 to 10 carbon atoms and 1 to 4 heteroatoms selected from oxygen, nitrogen, selenium, and sulfur (including oxides of sulfur, selenium and nitrogen) within the ring, and —C(O)O-heterocyclyl where the heterocyclyl group has from 1 to 8 carbon atoms and from 1 to 4 heteroatoms selected from nitrogen, sulfur, oxygen, selenium or phosphorous within the ring. Examples of acyloxy groups include acetoxy and propoxy;

optionally substituted ($C_6$-$C_{14}$ aryl)-($C_1$-$C_{10}$ alkyl) group. Preferably the aryl group is $C_6$-$C_{10}$ aryl. Preferably the alkyl group is $C_1$-$C_6$ alkyl, more preferably $C_1$-$C_3$ alkyl. Examples of substituted arylalkyl groups include benzyl, phenethyl, 1-hydroxybenzyl, and 1-thiobenzyl;

optionally substituted sulfinyl group selected from H—S(O)—, $C_1$-$C_{10}$ alkyl-S(O)— (preferably $C_1$-$C_6$ alkyl, more preferably $C_1$-$C_3$ alkyl), $C_3$-$C_8$ cycloalkyl-S(O)—, $C_6$-$C_{14}$ aryl-S(O)— (preferably, the aryl group has from 6 to 14 carbon atoms), heteroaryl-S(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)— where the heterocyclyl group has from 1 to 8 carbon atoms and from 1 to 4 heteroatoms selected from nitrogen, sulfur, oxygen, selenium or phosphorous within the ring. Examples of sulfinyl groups include methylsulfinyl, ethylsulfinyl, benzene sulfinyl (optionally substituted with methyl, methoxy, halogen, nitro, trifluoromethane or cyano), methoxysulfinyl, ethoxysulfinyl;

optionally substituted sulfonyl group selected from H—S(O)$_2$—, $C_1$-$C_{10}$ alkyl-S(O)$_2$— (preferably $C_1$-$C_6$ alkyl, more preferably $C_1$-$C_3$ alkyl), $C_3$-$C_8$ cycloalkyl-S(O)$_2$—, $C_6$-$C_{14}$ aryl-S(O)$_2$—, heteroaryl-S(O)$_2$— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$— where the heterocyclyl group has from 1 to 8 carbon atoms and from 1 to 4 heteroatoms selected from nitrogen, sulfur, oxygen, selenium or phosphorous within the ring. Examples of sulfonyl groups include methylsulfonyl, ethylsulfonyl, benzenesulfonyl (optionally substituted with methyl, methoxy, halogen, nitro, trifluoromethane or cyano), methoxycarbo, trifluoromethane;

optionally substituted oxyacylamino group of the formula —NR*C(O)OR* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of oxyacylamino groups include methoxycarbonylamido, and ethoxycarbonyl amido;

optionally substituted oxythioacyl group selected from HO—C(S)—, $C_1$-$C_{10}$ alkylO—C(S)— (preferably $C_1$-$C_6$ alkyl, more preferably $C_1$-$C_3$ alkyl), $C_3$-$C_8$ cycloalkylO—C(S)—, $C_6$-$C_{14}$ arylO—C(S)—, heteroarylO—C(S)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclylO—C(S)— where the heterocyclyl group has from 1 to 8 carbon atoms and from 1 to 4 heteroatoms selected from nitrogen, sulfur, oxygen, selenium or phosphorous within the ring. Examples of oxythioacyl groups include methoxythiocarbonyl and ethoxythiocarbonyl;

optionally substituted thioacyloxy group selected from H—C(S)—O—, $C_1$-$C_{10}$ alkyl-C(S)—O— (preferably $C_1$-$C_6$ alkyl, more preferably $C_1$-$C_3$ alkyl), $C_3$-$C_8$ cycloalkyl-C(S)—O—, $C_6$-$C_{14}$ aryl-C(S)—O—, heteroaryl-C(S)—O— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-C(S)—O— where the heterocyclyl group has from 1 to 8 carbon atoms and from 1 to 4 heteroatoms selected from nitrogen, sulfur, oxygen, selenium or phosphorous within the ring. Examples of thioacyloxy groups include thionoacetoxy and thionopropionoxy;

optionally substituted sulfinylamino group selected from H—S(O)—NR*—, $C_1$-$C_{10}$ alkyl-S(O)—NR*— (preferably the alkyl groups are $C_1$-$C_6$ alkyl, more preferably $C_1$-$C_3$ alkyl), $C_3$-$C_8$ cycloalkyl-S(O)—NR*—, $C_6$-$C_{14}$ aryl-S(O)—NR*—, heteroaryl-S(O)—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)—NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$cycloalkyl, $C_6$-$C_{14}$ aryl, heteroaryl having from 2 to 10 carbon atoms and 1 to 4 heteroatoms selected from nitrogen, sulfur, oxygen, selenium, and sulfur (including oxides of sulfur, selenium and nitrogen) within the ring, and heterocyclyl having from 1 to 8 carbon atoms and from 1 to 4 heteroatoms selected from nitrogen, sulfur, oxygen, selenium or phosphorous within the ring. Examples of sulfinylamino groups include methylsulfinylamino, ethylsulfinylamino, and benzenesulfinylamino (optionally substituted with methyl, methoxy, halogen, nitro, trifluoromethane or cyano);

amino group;

substituted amino groups of the formula —NR*R* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of substituted amino groups include residues of L-valine, D-valine, L-alanine, D-alanine, aspartic acid, and alanylserine, N-methylamino, and N,N'-dimethylamino;

optionally substituted sulfonylamino group selected from H—S(O)$_2$—NR*—, $C_1$-$C_{10}$ alkyl-S(O)$_2$—NR*— (preferably $C_1$-$C_6$ alkyl, more preferably $C_1$-$C_3$ alkyl), $C_3$-$C_8$ cycloalkyl-S(O)$_2$—NR*—, $C_6$-$C_{14}$ aryl-S(O)$_2$—NR*—, heteroaryl-S(O)$_2$—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$-NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of sulfonylamino groups include methylsulfonylamino, ethylsulfonylamino and benzene sulfonylamino (optionally substituted with methyl, methoxy, halogen, nitro, trifluoromethane or cyano);

optionally substituted oxysulfinylamino group selected from HO—S(O)—NR*—, $C_1$-$C_{10}$ alkylO—S(O)—NR*— (preferably $C_1$-$C_6$ alkyl, more preferably $C_1$-$C_3$ alkyl), $C_3$-$C_8$ cycloalkylO—S(O)—NR*—, $C_6$-$C_{14}$ arylO—S(O)—NR*—, heteroarylO—S(O)—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclylO—S(O)—NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of suitable oxysulfinylamino groups include methoxysulfinylamino and ethoxysulfinylamino;

optionally substituted oxysulfonylamino group selected from HO—S(O)$_2$—NR*—, $C_1$-$C_{10}$ alkylO—S(O)$_2$—NR*— (preferably $C_1$-$C_6$ alkyl, more preferably $C_1$-$C_3$ alkyl), $C_3$-$C_8$ cycloalkylO—S(O)$_2$—NR*—, $C_6$-$C_{14}$ arylO—S(O)$_2$—NR*—, heteroarylO—S(O)$_2$—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclylO—S(O)$_2$—NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of oxysulfonylamino groups include methoxysulfonylamino and ethoxysulfonylamino;

optionally substituted $C_2$-$C_{10}$ alkenyl group which may be straight chained or branched and have at least 1 or from 1-2 carbon to carbon double bonds. Preferably optionally substituted $C_2$-$C_6$ alkenyl. Examples of suitable optionally substituted alkenyl groups include ethenyl, n-propenyl, iso-propenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted $C_2$-$C_{10}$ alkynyl group having at least 1 or from 1-2 carbon to carbon triple bonds. Preferably $C_2$-$C_6$ alkynyl. Examples of suitable alkynyl groups include 1-propynyl, ethynyl, propargyl, pent-2-ynyl and trimethylsilylethynyl.

In some embodiments $R^{1C}$ is selected from the following groups:

$C_{1-3}$ alkoxy. Examples of suitable alkoxy groups include methoxy, ethoxy, n-propoxy, and iso-propoxy;

$C_{1-3}$ alkylthio. Examples of suitable alkylthio groups include methyl-S—, ethyl-S—, 1-thio-propyl, 2-thio-propyl and iso-propyl-S—;

$C_{1-3}$ alkylamino. Examples of suitable alkylamino groups include methylamino, ethylamino, 1-amino-propyl, 2-amino-propyl, and iso-propyl-amino; and $C_{1-3}$ dialkylamino. Examples of suitable alkylamino groups include dimethylamino, diethylamino, dipropylamino, ethylmethylamino, propylmethylamino, and propylmethylamino, where the alkyl groups may be straight chained or branched.

In some embodiments $R^{1D}$ is selected from a hydroxy group and an amino group.

In some embodiments L is selected from the following groups:

C=O,
O,
S,
SO,
SO$_2$,
Se,
SeO,
SeO$_2$,

C=NZ' where Z' is H, optionally substituted $C_1$-$C_{10}$ alkyl (preferably $C_1$-$C_6$, more preferably $C_1$-$C_3$), optionally substituted $C_6$-$C_{14}$ aryl or optionally substituted amino, or NR' where R' is selected from
H,
O, optionally substituted acyl group selected from H—C(O)—, $C_1$-$C_{10}$ alkyl-C(O)— (preferably $C_1$-$C_6$ alkyl, more preferably $C_1$-$C_3$ alkyl), $C_3$-$C_8$ cycloalkyl-C(O)—, $C_6$-$C_{14}$ aryl-C(O)—, heteroaryl-C(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring and heterocyclyl-C(O)— where the heterocyclyl group has from 1 to 8 carbon atoms and from 1 to 4 heteroatoms selected from nitrogen, sulfur, oxygen, selenium or phosphorous within the ring). Examples of acyl groups include formyl acetyl, propionyl, benzoyl (optionally substituted with methyl, methoxy, halogen, nitro, trifluoromethyl or cyano);

optionally substituted $C_2$-$C_{10}$ alkenyl group which may be straight chained or branched and have at least 1 or from 1-2 carbon to carbon double bonds. Preferably optionally substituted $C_2$-$C_6$ alkenyl. Examples of suitable optionally substituted alkenyl groups include ethenyl, n-propenyl, isopropenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted $C_1$-$C_{10}$ alkyl, preferably $C_1$-$C_6$ alkyl, more preferably $C_1$-$C_3$ alkyl. Examples of suitable alkyl groups include methyl, ethyl, 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

optionally substituted $C_6$-$C_{14}$ aryl;

optionally substituted $C_4$-$C_8$ cycloalkenyl;

optionally substituted $C_3$-$C_8$ cycloalkyl;

optionally substituted heteroaryl having from 2 to 10 carbon atoms and 1 to 4 heteroatoms selected from oxygen, nitrogen, selenium, and sulfur (including oxides of sulfur, selenium and nitrogen) within the ring optionally substituted heterocyclyl having from 1 to 8 carbon atoms and from 1 to 4 heteroatoms selected from nitrogen, sulfur, oxygen, selenium or phosphorous within the ring; or optionally substituted sulfonyl selected from H—S(O)$_2$—, $C_1$-$C_{10}$ alkyl-S(O)$_2$— (preferably $C_1$-$C_6$ alkyl, more preferably $C_1$-$C_3$ alkyl), $C_3$-$C_8$ cycloalkyl-S(O)$_2$—, $C_6$-$C_{14}$ aryl-S(O)$_2$—, heteroaryl-S(O)$_2$— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$— where the heterocyclyl group has from 1 to 8 carbon atoms and from 1 to 4 heteroatoms selected from nitrogen, sulfur, oxygen, selenium or phosphorous within the ring. Examples of sulfonyl groups include methylsulfonyl, ethylsulfonyl, benzenesulfonyl (optionally substituted with methyl, methoxy, halogen, nitro, trifluoromethane or cyano), methoxycarbo, trifluoromethane;

In some embodiments Q is selected from the following groups:

H;

CN;

halogen, preferably Br or Cl;

trialkylsilyl, in which each alkyl group is independently $C_1$-$C_{10}$ alkyl (preferably $C_1$-$C_6$ alkyl, more preferably $C_1$-$C_3$ alkyl);

optionally substituted $C_1$-$C_{10}$ alkyl (preferably $C_1$-$C_6$ alkyl, more preferably $C_1$-$C_3$ alkyl). Examples of suitable alkyl groups include methyl, ethyl, propyl, butyl, aminoalkyl, oxyacylaminoalkyl and oxysulphonylaminoalkyl;

optionally substituted $C_2$-$C_{10}$ alkenyl group which may be straight chained or branched and have at least 1 or from 1-2 carbon to carbon double bonds. Preferably optionally substituted $C_2$-$C_6$ alkenyl. Examples of suitable optionally substituted alkenyl groups include ethenyl, n-propenyl, isopropenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted $C_2$-$C_{10}$ alkynyl group having at least 1 or from 1-2 carbon to carbon triple bonds. Preferably $C_2$-$C_6$ alkynyl. Examples of suitable alkynyl groups include 1-propynyl, ethynyl, propargyl, pent-2-ynyl, trimethylsilylethynyl and 2-alkylethynyl.

optionally substituted oxyacyl selected from HOC(O)—, $C_1$-$C_{10}$ alkyl-OC(O)— (preferably preferably $C_1$-$C_6$ alkyl, more preferably $C_1$-$C_3$ alkyl), $C_3$-$C_8$ cycloalkyl-OC(O)—, $C_6$-$C_{14}$ aryl-OC(O)—, heteroaryl-OC(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-OC(O)— where the heterocyclyl group has from 1 to 8 carbon atoms and from 1 to 4 heteroatoms selected from nitrogen, sulfur, oxygen, selenium or phosphorous within the ring. Examples of oxyacyl groups include methoxycarbonyl, ethoxycarbonyl, propoxycarbonyl, butyloxycarbonyl, isobutyloxycarbonyl;

optionally substituted acyl group selected from H—C(O)—, $C_1$-$C_{10}$ alkyl-C(O)— (preferably $C_1$-$C_6$ alkyl, more preferably $C_1$-$C_3$ alkyl), $C_3$-$C_8$ cycloalkyl-C(O)—, $C_6$-$C_{14}$ aryl-C(O)—, heteroaryl-C(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring and heterocyclyl-C(O)— where the heterocyclyl group has from 1 to 8 carbon atoms and from 1 to 4 heteroatoms selected from nitrogen, sulfur, oxygen, selenium or phosphorous within the ring). Examples of acyl groups include formyl acetyl, propionyl, benzoyl (optionally substituted with methyl, methoxy, halogen, nitro, trifluoromethyl or cyano);

optionally substituted acylamino of the formula —NR*C(O)R* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring;

optionally substituted aminoacylamino, of the formula —NR*C(O)NR*R* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring;

OR", where R" is selected from H or an optionally substituted $C_1$-$C_{10}$ alkyl (preferably $C_1$-$C_6$ alkyl, more preferably $C_1$-$C_3$ alkyl). Examples of suitable OR groups include hydroxy, methoxy, ethoxy, n-propoxy, iso-propoxy, n-butoxy, tert-butoxy, sec-butoxy, n-pentoxy, n-hexoxy and 1,2-dimethylbutoxy;

NR'R', preferably R is selected from H, heteroaryl having from 2 to 10 carbon atoms and 1 to 4 heteroatoms selected from oxygen, nitrogen, selenium, and sulfur (including oxides of sulfur, selenium and nitrogen) within the ring, amino, amino$C_1$-$C_{10}$ alkyl (preferably $C_1$-$C_6$ alkyl, more preferably $C_1$-$C_3$ alkyl), hydroxyl, hydroxy$C_1$-$C_{10}$ alkyl (preferably $C_1$-$C_6$ alkyl, more preferably $C_1$-$C_3$ alkyl), $C_1$-$C_{10}$ alkoxy (preferably $C_1$-$C_6$ alkoxy, more preferably $C_1$-$C_3$ alkoxy), $C_1$-$C_{10}$alkoxy $C_1$-$C_{10}$alkyl, oxyacyl, oxyacylalkyl, oxyacylamino, oxyacylaminoalkyl, guanidine, guanidinoalkyl or an optionally substituted $C_1$-$C_{10}$ alkyl group (preferably $C_1$-$C_6$ alkyl, more preferably $C_1$-$C_3$ alkyl). Examples of suitable N"R" groups include $NH_2$, alkylamino, dialkylamino, heteroarylamino, aminoalkylamino, hydroxyalkylamino, alkoxyalkylamino, oxyacylalkylamino, oxyacylaminoalkylamino, guanidinoalkylamino;

SR", preferably R" is selected from H, heteroaryl having from 2 to 10 carbon atoms and 1 to 4 heteroatoms selected from oxygen, nitrogen, selenium, and sulfur (including oxides of sulfur, selenium and nitrogen) within the ring, amino, amino$C_1$-$C_{10}$ alkyl (preferably $C_1$-$C_6$ alkyl, more preferably $C_1$-$C_3$ alkyl), hydroxyl, hydroxy$C_1$-$C_{10}$ alkyl (preferably $C_1$-$C_6$ alkyl, more preferably $C_1$-$C_3$ alkyl), $C_1$-$C_{10}$ alkoxy (preferably $C_1$-$C_6$ alkoxy, more preferably $C_1$-$C_3$ alkoxy), $C_1$-$C_{10}$alkoxy $C_1$-$C_{10}$alkyl, oxyacyl, oxyacylalkyl, oxyacylamino, oxyacylaminoalkyl, guanidine, guanidinoalkyl or an optionally substituted $C_1$-$C_{10}$ alkyl group (preferably $C_1$-$C_6$ alkyl, more preferably $C_1$-$C_3$ alkyl). Examples of suitable S'R" groups include alkylthio, aminoalkylthio, heteroarylthio, aminoalkylthio, hydroxyalkylthio, alkoxyalkylthio, oxyacylalkylthio, oxyacylaminoalkylthio, guanidinoalkylthio;

hydrazine.

In the definitions of the groups X, $R^{1A}$-$R^{1B}$, Q, L and $R^{2A}$-$R^{2E}$, the term "optionally substituted" refers to a group which may or may not be further substituted or fused (so as to form a condensed polycyclic group) with one or more groups selected from hydroxy, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocyclyloxy, oxyacyl, oxime, oxime ether, hydrazone, —NHC(NH)$NH_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like.

In one embodiment $R^{2D}$, $R^{2C}$, and $R^{2B}$ are methoxy and L is a carbonyl group (C=O).

Accordingly, in this embodiment the TPIs are represented by formula (Ia) or salts, solvates, or prodrugs thereof

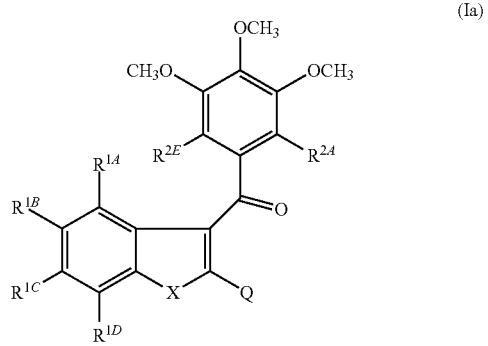

(Ia)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

$R^{2A}$ and $R^{2E}$ independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In another embodiment, $R^{1A}$, $R^{1B}$, $R^{2A}$ and $R^{2E}$ represent H and $R^{1C}$, $R^{2B}$, $R^{2C}$ and $R^{2D}$ represents $C_{1-3}$ alkoxy.

Accordingly, in this embodiment the TPI is represented by formula (Ib) or salts, solvates or prodrugs thereof

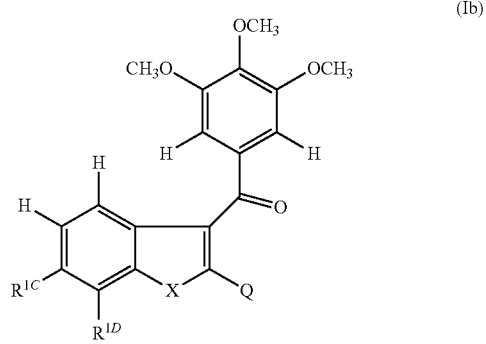

(Ib)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy;

$R^{1D}$ represents hydroxy or amino;

Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In a preferred embodiment $R^{1C}$ represents methoxy.

For the compounds represented by formulae I, Ia and Ib, X is preferably selected from O, S and NR. More preferably X is O or NR and most preferably X is O.

Accordingly, in another embodiment the TPI is represented by formula II:

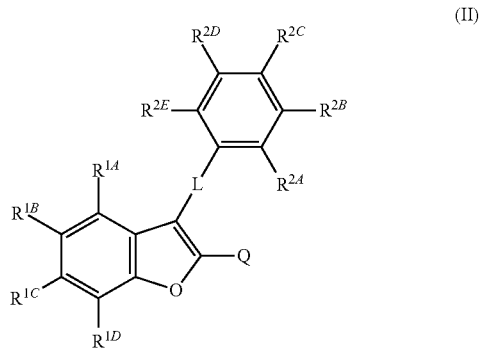

(II)

wherein;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

In this embodiment it is preferred that L is a carbonyl group (C=O). Also, preferably at least one of $R^{2D}$, $R^{2C}$ or $R^{2B}$ represents a hydroxy or $C_{1-3}$ alkoxy group. More preferably when X=O, L is a carbonyl group an $R^{2D}$, $R^{2C}$ and $R^{2B}$ represent methoxy. Even more preferably when X=O, L is a carbonyl group, $R^{2D}$, $R^{2C}$, and $R^{2B}$ represent methoxy and $R^{1A}$, $R^{1B}$, $R^{2A}$, $R^{2E}$ are H.

Furthermore, for the compounds of formula (I), (Ia), (Ib) and (II) it is preferred that Q represents H, CN, optionally substituted $C_{2-4}$ alkynyl, optionally substituted $C_{2-6}$ alkenyl, optionally substituted $C_{1-4}$ alkyl, hydroxy, optionally substituted oxyacyl, NR"R", SR" (where each R" is independently H, optionally substituted $C_{1-4}$alkyl, optionally substituted heterocyclyl, optionally substituted heteroaryl), NR'"NR'" (where each R'" is independently H, $C_{1-3}$ alkyl), optionally substituted acylamino, or halogen.

In some embodiments Q is independently selected from the following groups:
H;
CN;
halogen, preferably Br or Cl;
alkyl group, preferably methyl, ethyl, propyl, butyl;
substituted alkyl group, preferably amino, oxyacylaminoalkyl and oxysulphonylaminoalkyl;

optionally substituted alkenyl, preferably ethenyl, 2-alkylethenyl, 2-oxyacylethenyl, 2-aminoacylethenyl;
optionally substituted alkynyl, preferably ethynyl, 2-alkylethynyl;
optionally substituted oxyacyl;
OR", preferably hydroxy, methoxy, ethoxy;
NR"R", preferably $NH_2$, alkylamino, dialkylamino, heteroarylamino, aminoalkylamino, hydroxyalkylamino, alkoxyalkylamino, oxyacylalkylamino, oxyacylaminoalkylamino, guanidinoalkylamino;
SR", preferably alkylthio, aminoalkylthio, heteroarylthio, aminoalkylthio, hydroxyalkylthio, alkoxyalkylthio, oxyacylalkylthio, oxyacylaminoalkylthio, guanidinoalkylthio; hydrazine.

In a further preferred embodiment the TPI for use in the present method is a compound of formula (III) or a salt, solvate or prodrug thereof

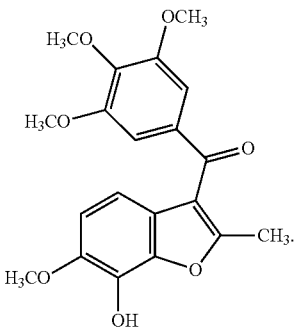 [SMILES: COc1cc(C(=O)c2c(C)oc3c(O)c(OC)ccc23)cc(OC)c1OC]

In an embodiment, the compound of formula (I), (Ia), (Ib), (II) or (III) is a prodrug selected from an ester, an acetate, a phosphate ester or an amide prodrug. In another embodiment, the compound of formula (I) (Ia), (Ib), (II) or (III) is a phosphate prodrug. In a particular embodiment, $R^{1D}$ is hydroxy and the prodrug is a phosphate ester of the hydroxy group. Preferably, the phosphate ester is a disodium phosphate ester.

The compound of formula (III) (2-Methyl-7-hydroxy-3-(3,4,5-trimethoxybenzoyl)-6-methoxybenzofuran) can be prepared by the synthetic methodology described in PCT/AU2007/000101 (WO 07/087684).

The compounds of formula I, Ia, Ib, II or III have been observed to be potent tubulin polymerisation inhibitors (TPIs). An important aspect of the compounds of formulae I, Ia, Ib, II and III is the combination of the specific C-6 and C-7 substituents together with the C-2 Q-group (especially C-2 methyl) which appears to confer greater potency and selectivity when compared to other structurally related TPI compounds. In these compounds selectivity is not simply reliant on the predisposition of tumour vasculature towards collapse when challenged with the VDA but on a capacity of the VDA to distinguish between tumour endothelial cells and normal endothelial cells. Normal endothelial cells, found in healthy tissues, are in a "quiescent" state and tumour endothelial cells are in an "activated" state. Most VDAs do not distinguish between these two states, for example, Combretastatin A4 (CA4) is equally potent against quiescent and activated endothelial cells. However, the compounds of formulae I, Ia, Ib, II and particularly III show selectivity towards tumor endothelial cells (activated) over normal endothelial cells (quiescent).

In some embodiments, the TPI for use in the present method is a compound of formula I, Ia, Ib or II or a salt, solvate or prodrug thereof wherein $R^{1C}$ is $C_{1-3}$ alkoxy, $R^{1D}$ is hydroxyl and Q is optionally substituted $C_{1-10}$ (or $C_{1-6}$ or $C_1$-3) alkyl.

The TPI compounds of formula I, Ia, Ib, II or III may be prepared by known methods including those disclosed in WO 02/060872 and WO 07/087684 which are incorporated herein by reference.

It will be appreciated that the TPIs and compounds of formula I, Ia, Ib, II, or III can be administered to a subject as a pharmaceutically acceptable salt thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

It will also be appreciated that any compound that is a prodrug of a TPI or a compound of formula I, Ia, Ib, II, and III are also within the scope of the invention. The term "pro-drug" is used in its broadest sense and encompasses those derivatives that are converted in vivo to the compound (for instance, a compound of formulae I, Ia, Ib, II, and III). Such derivatives would readily occur to those skilled in the art, and include, for example, compounds where the free hydroxy group (for instance at C-7 position or RID) is converted into an ester, such as an acetate or phosphate ester, or where a free amino group (for instance at C-7 position or $R^{1D}$) is converted into an amide (e.g., α-aminoacid amide). Procedures for esterifying, for example, acylating, the compounds are well known in the art and may include treatment of the compound with an appropriate carboxylic acid, anhydride or chloride in the presence of a suitable catalyst or base. A particularly preferred prodrug is a disodium phosphate ester. The disodium phosphate ester (in particular a C-7 disodium phosphate ester of a compound of formula III) of the compound may be useful in increasing the solubility of the compounds. This, for instance, may allow for delivery of the compound in a benign vehicle like saline. The disodium phosphate ester may be prepared in accordance with the methodology described in Pettit, G. R., et al, *Anticancer Drug Des.,* 1995, 10, 299. Other texts which generally describe prodrugs (and the preparation thereof) include: *Design of Prodrugs,* 1985, H. Bundgaard (Elsevier); *The Practice of Medicinal Chemistry,* 1996, Camille G. Wermuth et al., Chapter 31 (Academic Press); and *A Textbook of Drug Design and Development,* 1991, Bundgaard et al., Chapter 5, (Harwood Academic Publishers).

In some embodiments, the TPI for use in the present method is a compound of formula (IV)

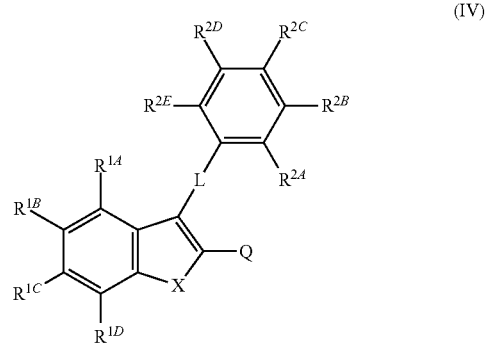

wherein, X, $R^{1A}$-$R^{1C}$ and $R^{2A}$-$R^{2E}$, L and Q are as defined in formula I, Ia, Ib, II or III, and $R^{1D}$ is $OR^3$ or $NHR^3$, and $R^3$ is H or an ester. When $R^3$ is an ester, the ester may consist of a carbonyl adjacent to an ether linkage (such as an acetate ester), or may be an inorganic ester (such as a phosphate, sulfate, nitrate or borate ester). In some embodiments, the ester is an acetate or a phosphate ester. A particularly preferred ester is a disodium phosphate ester.

The compounds of formulae I, Ia, Ib, II, III and IV (or a salt or prodrug thereof) may be in crystalline form either as the free compound or as a solvate (e.g. hydrate) and it is intended that both forms are within the scope of the present invention. Methods of solvation are generally known within the art.

Chemical Definitions

"Alkyl" refers to monovalent alkyl groups which may be straight chained or branched and preferably have from 1 to 10 carbon atoms or more preferably 1 to 6 carbon atoms, and even more preferably 1 to 3 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms, and even more preferably 1 to 3 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

"Aryl" refers to an unsaturated aromatic carbocyclic group having a single ring (eg., phenyl) or multiple condensed rings (eg., naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH=CH—), and the propenylene isomers (e.g., —CH$_2$CH=CH— and —C(CH$_3$)=CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacylamino" refers to the group —NR*C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR*C(O)R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR*-alkyl, —OC(O)NR*-aryl, —OC(O)NR*-heteroaryl, and —OC(O)NR*-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR*C(O)O-alkyl, —NR*C(O)O-aryl, —NR*C(O)O-heteroaryl, and NR*C(O)O-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O— heteroaryl, and —OC(O)O-heterocyclyl where alkyl, cycloalkyl, aryl, heteroaryl, and heterocyclyl are as described herein.

"Acylimino" refers to the groups —C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR*)—OR* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (ie. contains 4n+2π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg., pyridyl, pyrrolyl or N-oxides thereof or furyl) or multiple condensed rings (eg., indolizinyl, benzoimidazolyl, coumarinyl, quinolinyl, isoquinolinyl or benzothienyl).

"Heterocyclyl" refers to a monovalent saturated or unsaturated group having a single ring or multiple condensed rings, preferably from 1 to 8 carbon atoms and from 1 to 4 heteroatoms selected from nitrogen, sulfur, oxygen, selenium or phosphorous within the ring. The most preferred heteroatom is nitrogen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR*—P(O)(R)(OR*) where R* represents H, alkyl, cycloalkyl, alkenyl, or aryl, R represents OR* or is hydroxy or amino and R*** is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR*—, alkyl-S(O)—NR*—, cycloalkyl-S(O)—NR*—, aryl-S(O)—NR*—, heteroaryl-S(O)—NR*—, and heterocyclyl-S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR*—, alkyl-S(O)$_2$—NR*—, cycloalkyl-S(O)$_2$—NR*—, aryl-S(O)$_2$—NR*—, heteroaryl-S(O)$_2$—NR*—, and heterocyclyl-S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR*—, alkylO—S(O)—NR*—, cycloalkylO—S(O)—NR*—, arylO—S(O)—NR*—, heteroarylO—S(O)—NR*—, and heterocyclylO—S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR*—, alkylO—S(O)$_2$—NR*—, cycloalkylO—S(O)$_2$—NR*—, arylO—S(O)$_2$—NR*—, heteroarylO—S(O)$_2$—NR*—, and heterocyclylO—S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R*R*N—C(S)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR*—, alkyl-C(S)—NR*—, cycloalkyl-C(S)—NR*—, aryl-C(S)—NR*—, heteroaryl-C(S)—NR*—, and heterocyclyl-C(S)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R*R*N—S(O)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R*R*N—S(O)$_2$—, where each R* is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxy, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocyclyloxy, oxyacyl, oxime, oxime ether, hydrazone, —NHC(NH)NH$_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like. An optionally substituted amino group may also include amino acid and peptide residues.

mTOR Inhibitors

In one embodiment of the invention, the method of the invention is predictive of patient response to treatment with a vascular disrupting agent in combination with an mTOR inhibitor. The mechanistic target of rapamycin (mTOR serine/threonine kinase), also known as mammalian target of rapamycin, mTOR, or FK506-binding protein 12-rapamycin-associated protein 1 (FRAP1), is a serine/threonine protein kinase that regulates cell growth, cell proliferation, cell motility, cell survival, protein synthesis, and transcription. MTOR belongs to the phosphatidylinositol 3-kinase-related kinase protein family. PI3K/Akt-dependent phosphorylation signals through tuberin, the protein product of the TSC1/TSC2 complex, leading to mTOR activation. mTOR subsequently phosphorylates downstream targets, causing initiation of protein translation. Accordingly, any agent that inhibits the activation of mTOR, causing down-regulation of its downstream targets, is encompassed by the meaning of "mTOR inhibitor" as used herein.

Examples of mTOR inhibitors include BEZ235 (NVP-BEZ235), deforolimus (AP 23573, MK-8669), PI-103, rapamycin (Sirolimus, Rapamune), temsirolimus (Toricel, CCI-779), everolimus (Afinitor, RAD001, Certican), ABT 578, SAR 543 and AP 23841. In one particular embodiment, the mTOR inhibitor is everolimus (Afinitor).

Dosing and Administration

In one embodiment, a patient identified as having an increased likelihood of responding to treatment is administered a vascular disrupting agent. Daily dosages for the vascular disrupting agent will, of course, vary depending on a variety of factors, e.g., the compound chosen, the particular condition to be treated and the desired effect. In general, however, satisfactory results are achieved on administration at daily dosage rates of about 0.05 to 20 mg/kg per day, particularly 1 to 20 mg/kg per day, e.g. 0.4 to 16 mg/kg per day, as a single dose or in divided doses. The vascular disrupting agent may be administered by any conventional route, in particular parenterally, e.g., in the form of injectable solutions or suspensions, or enterally, e.g., orally, e.g., in the form of tablets, capsules, drink solutions. Suitable unit dosage forms for oral administration comprise from about 0.02 to 50 mg active ingredient, usually 0.1 to 30 mg and 2 to 25 mg, 4 to 20 mg e.g. together with one or more pharmaceutically acceptable diluents or carriers therefore.

For instance, an administration regime may include adding the vascular disrupting agent (e.g., compound of formula I, Ia, Ib, II, or III) at an assigned dose level by I.V. on days 1 and 8 (of a 21 day cycle). In this embodiment the compound of formula (III) may be dosed at a level of between 4 to 16 mg/kg.

Thus, while the skilled person will readily be able to determine suitable doses of the vascular disrupting agent, in one embodiment, BNC105P is administered at a dosage of about 8 mg/m$^2$ to about 16 mg/m$^2$. In one particular embodiment, BNC105P is administered at a dosage of 16 mg/m$^2$ on day 1 and day 8 of a 21 day treatment cycle. As understood in the art, the patient may receive multiple cycles of treatment.

In one embodiment, the patient is treated with a combination therapy comprising a vascular disrupting agent and another therapeutic. As understood in the art, the terms "combination therapy", "combination treatment", or "pharmaceutical combination" refer to the use of more than one medication or other therapy (vs. monotherapy, which is any therapy taken alone), to treat a single disease. A "Pharmaceutical combination" therapy, for example, may be achieved by prescribing/administering separate drugs, or, where available, dosage forms that contain more than one active ingredient (such as fixed-dose combinations).

The methods and uses of the present invention encompass the administration of the an additional therapeutic agent or a salt, solvate or prodrug thereof (combination partner a) in combination with a vascular disrupting agent or a salt, solvate or prodrug thereof (combination partner b) to a single patient, and is intended to include treatment regimens in which the agents are not necessarily administered by the same route of administration or at the same time. Accordingly, combination partners (a) and (b) may be administered together, one after the other or separately in one combined unit dosage form or in two separate unit dosage forms. The unit dosage form may also be a fixed combination such as a pharmaceutical composition which comprises both partner (a) (or a salt, solvate or prodrug thereof) and partner (b) (or a salt, solvate or prodrug thereof).

In particular, a therapeutically effective amount of each of the combination partner of the combination of the invention may be administered simultaneously or sequentially and in any order, and the components may be administered separately or as a fixed combination.

For example, the method of the invention may comprise: (i) administration of partner (a) in free or pharmaceutically acceptable salt form; and (ii) administration of partner (b) in free or pharmaceutically acceptable salt form, simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that converts in vivo to the combination partner as such.

In one embodiment, the patient is treated with a combination of a vascular disrupting agent and an mTOR inhibitor. Examples of mTOR inhibitors suitable for use in the present invention include BEZ235 (NVP-BEZ235), deforolimus (AP 23573, MK-8669), PI-103, rapamycin (Sirolimus, Rapamune), temsirolimus (Toricel, CCI-779), everolimus (Afinitor, RAD001, Certican), ABT 578, SAR 543 and AP 23841. In one particular embodiment, the mTOR inhibitor is everolimus (Afinitor). In one particular embodiment, the patient is administered a vascular disrupting agent in combination with everolimus.

In one embodiment, everolimus is administered daily to the patient.

In another embodiment, BNC105P is administered to the patient in weekly doses. In one particular embodiment, everolimus is administered daily to the patient, and BNC105P is administered to the patient after about 5, 6, 7, 8 or 9 days of everolimus administration and again at about 13, 14, 15, 16, or 17 days of everolimus administration. In one embodiment, the everolimus is administered daily at a dosage of 10 mg.

Additional Therapies

The methods of the present invention may utilise the combination of a vascular disrupting agent in conjunction with other therapeutic agents and treatment modalities such as tumor irradiation. For example, the combination therapy of the present invention may be used in conjunction with another chemotherapeutic, antibody and or immunotherapeutic that is suitable for administration to a patient for the treatment of cancer.

Examples of therapeutic agents that may be administered in conjunction with the combination of a vascular disrupting agent include mTOR inhibitors, tyrosine kinase inhibitors, such as VEGF-directed tyrosine kinase inhibitors and proteasome inhibitors. By way of example, tyrosine kinase inhibitors include sunitinib (Sutent), sorafenib (Nexavar), axitinib (Inlyta) and pazopanib (Votrient). Another therapeutic agent used in the treatment of cancer is carfilzomib (Kyprolis), a selective proteasome inhibitor. By way of non-limiting examples, immunotherapeutic agents useful in the invention include interleukin 2 (IL2), and interferon alpha (IFNα). One non-limiting example of a suitable therapeutic antibody that may be used is bevacizumab (Avastin).

EXAMPLES

Example 1. Disruptor-1 Trial: Study of BNC105P in Combination with Everolimus for Metastatic Clear Cell Renal Cell Carcinoma The objective of the study was to determine the response rate of patients administered BNC105P (vascular disrupting agent) in combination with everolimus (mTOR inhibitor) in patients who had progressed from prior tyrosine kinase inhibitor therapy. In addition, the present inventors determined the improvement in 6-months progression free survival (PFS) with the addition of BNC105P to everolimus (Afinitor). A control group of patients received everolimus alone.

The medical histories of patients were obtained prior to commencement of the study. Patients selected for the study exhibited a Karnofsky Performance Score of ≥70, had metastatic or locally advanced inoperable renal cell carcinoma, had progressive disease after 1-2 prior treatments with VEGF-directed tyrosine kinase inhibitors, had no active brain metastases, and good bone marrow, liver and kidney function.

Patients in the BNC105P in combination with everolimus study group (the "combination arm") were administered 10 mg oral everolimus daily. On days 1 and 8 of the 21 day cycle period, the patients were administered 16 mg/m$^2$ BNC105P, which had been determined to be the maximum tolerated dose, by intravenous infusion over a 10 minute period (FIG. 1). Treatment was continued until disease progressed, intolerable toxicity became apparent, or until consent was withdrawn. A control group of patients were administered with everolimus alone.

All patients in the study were followed for disease progression and survival. Prior to commencing treatment, patients enrolled in the study were subject to disease assessment including: CT of chest, abdomen and pelvis; CT of the head or brain MRI; bone scan; echocardiography (ECHO) or multiple gated acquisition scan (MUGA). At every 3 cycles of treatment, CT scans of chest, abdomen and pelvis, and bone scans, were performed to determine disease progression.

Example 2. Disease Evaluation and Response Criteria

The criteria for disease evaluation included:
Measurable disease:—the presence of at least one measurable lesion. If the measurable disease is restricted to a solitary lesion, its neoplastic nature should be confirmed by cytology/histology.

Measurable lesions:—lesions that can be accurately measured in at least one dimension with longest diameter (LD)>20 mm using conventional techniques or >10 mm with spiral CT scan.

Non-measurable lesions:—all other lesions, including small lesions (longest diameter <20 mm with conventional techniques or <10 mm with spiral CT scan), i.e., bone lesions, leptomeningeal disease, ascites, pleural/pericardial effusion, inflammatory breast disease, lymphangitis cutis/pulmonis, cystic lesions, and also abdominal masses that are not confirmed and followed by imaging techniques.

Baseline documentation of "target" and "non-target" lesions:—all measurable lesions up to a maximum of five lesions per organ and 10 lesions in total, representative of all involved organs should be identified as target lesions and recorded and measured at baseline. Target lesions should be selected on the basis of their LD. The baseline sum LD will be used as reference by which to characterize the objective tumor. All other lesions (or sites of disease) should be identified as non-target lesions and should also be recorded at baseline. Measurements of these lesions are not required, but the presence or absence of each should be noted throughout follow-up.

The response criteria for the evaluation of target lesions were as follows:

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started The response criteria for the evaluation of non-target lesions were as follows:

Complete Response (CR) Disappearance of all non-target lesions and normalization of tumor marker level Incomplete Response/Stable Disease (SD): Persistence of one or more non-target lesion(s) or/and maintenance of tumor marker level above the normal limits Progressive Disease (PD): Appearance of one or more new lesions and/or unequivocal progression of existing non-target lesions Time to disease progression was determined as a measurement from the start of the treatment until the criteria for disease progression is met (or death occurs), taking as reference the smallest measurements recorded since the treatment started. The time to progression, in patients with documented disease progression at their first disease evaluation, were considered the time between initiation of therapy and the date of first documentation of disease progression.

Example 3. Biological Sample Processing

Human EDTA plasma samples were taken from patients to quantitatively measure the concentration of 56 analytes from the Human CustomMAP at Myriad RBM (MRBM). All samples were received, processed and stored according to established MRB procedures. The samples were thawed at room temperature, vortexed, centrifuged for clarification and adequate volume was removed for Human CustomMAP analysis and plated into a master microtiter plate.

Multi-Analyte Profile (MAP) Technology

MRBM has developed species-specific MAPs based on Luminex technology with capability to simultaneously measure multiple biochemical markers in a very small sample volume. Luminex technology performs up to 100 multiplexed, microsphere-based assays in a single reaction vessel by combining optical classification schemes, biochemical assays, flow cytometry and advanced digital signal processing hardware and software.

Multiplexing is accomplished by assigning each analyte-specific assay a microsphere set labelled with a unique fluorescence signature. To attain 100 distinct microsphere signatures, two fluorescent dyes, red and far red, are mixed in various combinations using ten intensity levels of each dye (i.e., 10×10). Each batch or set of microspheres is encoded with a fluorescent signature by impregnating the microspheres with one of these dye combinations.

After the encoding process, an assay-specific capture reagent (i.e., antigens, antibodies, receptors, peptides, enzyme substrates, etc.) is conjugated covalently to each unique set of microspheres. Covalent attachment of the capture reagent to the microspheres is achieved with standard carbodiimide chemistry using carboxyl functional groups located on the surface of each 5.6 μm microsphere and primary amines within the capture reagent. Coupling chemistry is performed on large numbers of individual microspheres ($10^7$-$10^9$ microspheres/mL) simultaneously within each unique set, resulting in low microsphere-to-microsphere variability.

After optimizing the parameters of each assay separately, Multi-Analyte Profiles are performed by mixing up to 100 different sets of the microspheres in a single well of a 96- or 384-format microtiter plate. A small sample volume is added to the well and allowed to react with the microspheres. The assay-specific capture reagent on each individual microsphere binds the analyte of interest. A cocktail of assay-specific, biotinylated detecting reagents (e.g., antigens, antibodies, ligands, etc.), is reacted with the microsphere mixture, followed by a streptavidin-labeled fluorescent "reporter" molecule (typically phycoerythrin). Because the microspheres are in suspension, the assay kinetics are near solution-phase. Finally, the multiplex is washed to remove unbound detecting reagents.

After washing, the mixture of microspheres is analyzed using the Luminex 100/200™ instrument. Similar to a flow cytometer, the instrument uses hydrodynamic focusing to pass the microspheres in single file through two laser beams.

As each individual microsphere passes through the excitation beams, it is analyzed for size, encoded fluorescence signature and the amount of fluorescence generated in proportion to the analyte. Microsphere size, determined by measuring the 90-degree light scatter as the microspheres pass through a red diode laser (633 nm), is used to eliminate microsphere aggregates from the analysis. While in the red excitation beam, the encoded red and far red dyes are excited and the resulting fluorescence signature (ratio 660 nm/720 nm) is filtered, measured using avalanche photodiodes, and classified to a microsphere set. Since each microsphere is encoded with a unique signature, the classification identifies the analyte being measured on that individual microsphere. As the microsphere passes through a green diode-pumped solid state laser (532 nm), a fluorescence "reporter" signal (580 nm) is generated in proportion to the analyte concentration, filtered and measured using a photomultiplier tube.

Luminex Testing

Using automated pipetting on Tecan robots, an aliquot of each sample was introduced into one of the capture microsphere multiplexes of the Human CustomMAP. These mixtures of sample and capture microspheres were thoroughly mixed and incubated at room temperature for 1 hour. Multiplexed cocktails of biotinylated, reporter antibodies for each multiplex were then added robotically and after thorough mixing, were incubated for an additional hour at room temperature.

Multiplexes were developed using an excess of streptavidin-phycoerythrin solution which was thoroughly mixed into each multiplex and incubated for 1 hour at room temperature. The volume of each multiplexed reaction was reduced by vacuum filtration and the volume increased by dilution into matrix buffer for analysis. Analysis was performed in a Luminex instrument and the resulting data stream was interpreted using data analysis software.

Assays were run in high density multiplexed panels and the Least Detectable Dose (LDD) was determined as the mean +3 standard deviations of 20 blank readings. The LLOQ is determined by the concentration of an analyte where the measurement of analyte demonstrates a coefficient of variation (CV) of 30%. It represents the lowest concentration of analyte that can be measured with a precision better than or equal to 30%. Appropriate dilutions were made to ensure a quantitative measurement within the limits of the assay.

An eight (n=8) point standard curve (S1-S8) was used to obtain quantitative measurements for each sample. Quality Controls (QC's) (n=3; C1-C3) were run in duplicate along different points of the curve to ensure both accuracy and precision for each analyte.

Chemicals and Solutions

Streptavidin-Phycoerythrin was purchased from Molecular Probes™. All buffers, reagents, capture microsphere multiplexes of the Human CustomMAP, multiplexed cocktails of biotinylated reporter antibodies, and multiplexed standards and controls were prepared by MRBM.

Example 4: Methods of Evaluation and Statistical Analysis

Data acquisition, analysis and reporting (MRBM Plate Viewer) were performed in real-time on all microsphere sets included in the MAP. A minimum of twenty individual microspheres from each unique set were analyzed and the median value of the analyte-specific, or "reporter," fluorescence were logged. Using calibrators and assay controls, specific, sensitive, and quantitative results were achieved with precision enhanced by the analysis of at least twenty microspheres per data point.

All safety analyses were performed using the Intent-To-Treat (ITT) population. The standard summary statistics for continuous variables were: mean, standard deviation, median, quartiles, maximum and minimum. The standard summary statistics for discrete values were: count and proportion. Progression free survival (PFS) was defined as date on study to date of disease progression or death, and overall survival of patients was summarized by Kaplan-Meier methods performed among the ITT population.

The 6-month PFS and response rates among evaluable patients were summarized by proportions together with 95% confidence intervals. Counts and proportions by toxicity were presented with exact binomial 95% confidence intervals for the following (ITT population).

The biomarker levels at each time and the change in biomarker levels were examined. The mean change from pre- to post-infusion was calculated as the mean of C1D1 pre-infusion minus C1D1 post-infusion. Thus, a positive mean change from pre- to post-infusion indicates a reduction in the biomarker over infusion time.

Example 5. Results

There were 56 biomarkers. For 10 of the biomarkers, all samples values were below the limit of detection of the assay so no analyses were possible. An additional 2 biomarkers had many values below the detectable limit of the assay so the analysis with progression by 6 months was unable to be performed. The present inventors correlated biomarker changes induced by BNC105P infusion with progression free survival. The dosing schedule and biomarker sampling time points are provided in FIG. 1.

Biomarkers were analysed to determine those which exhibited a statistically significant association between biomarker plasma concentration change and progression free survival. BNC105P-induced biomarker plasma concentration changes were detectable after the initial administration of BNC105P on Cycle 1/Day 1 (C1D1), both at the 1 hour post-administration sampling time and at 3 hours post administration sampling time.

The five biological markers for which a change in concentration pre-administration versus post-administration was detected were Serum Amyloid P-Component (SAP), Sex Hormone-Binding Globulin (SHBG), Myoglobin (MB), Matrix Metalloproteinase-9 (MMP-9), and Stem Cell Factor (SCF). Analysis of the change in biomarker levels is shown in Table 2.

TABLE 2

BNC105P induced changes in Plasma Biomarkers correlate with 6 month Progression Free Survival

|  | Median Post/Baseline Ratio | Correlation with PFS (P value) | Biomarker change Ratio Range associated with better PFS |
|---|---|---|---|
| SAP | 0.95 | 0.0184 | ≤0.95 |
| SHBG | 0.92 | 0.0063 | ≤0.92 |
| Myoglobin | 0.935 | 0.0011 | ≤0.935 |
| MMP-9 | 1.060 | 0.042 | >1.060 |
| SCF | 1.0 | 0.0291 | >1 |

The ratio of post-versus pre-administration levels of the biological markers listed in Table 1 are shown in FIGS. 2A, 3A, 4A, 5A and 6A. Samples were taken from patients at both 1 hour and 3 hours post administration with BNC105P and exhibited consistent changes in marker level at both time points. The median level of the biological markers at each time point in these Figures is indicated with a solid line.

FIGS. 2B, 3B, 4B, 5B and 6B demonstrate that patients separated into two groups based on the median of the ratio of biomarker post administration with BNC105P versus the baseline (pre-administration) level of the biomarker. From these Figures, it can be seen that the patient population that exhibited a decrease in levels of SAP, SHBG or Myoglobin following administration with BNC105P had greater progression free survival compared to rest of the patient population. In contrast, the patient population that had an increase in the level of MMP-9 or SCF following administration with BNC105P had greater progression free survival compared to the rest of the patient population.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from AU 2014902541 filed 2 Jul. 2014, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Gershagen et al. (1989) Nucleic Acids Res, 17:9245-9258
Mantzouranis et al. (1985) J Biol Chem, 260:7752-7756
Metzker (2010) Nat Rev Genet, 11(1):31-46

The invention claimed is:

1. A method of treating cancer in a patient, the method comprising:

identifying a patient having a level of a biological marker prior to administration with a vascular disrupting agent which is different to the level of the biological marker following administration with the vascular disrupting agent, wherein the biological marker is selected from Serum Amyloid P (SAP), Sex Hormone-Binding Globulin (SHBG), Myoglobin, and/or Stem Cell Factor (SCF), and administering the vascular disrupting agent to the patient, wherein a level of a biological marker prior to administration with the vascular disrupting agent that is different to the level of the biological marker following administration with the vascular disrupting agent is indicative of the patient responding to treatment with the vascular disrupting agent, and wherein the vascular disrupting agent is a compound of formula (I) or a salt, solvate or prodrug thereof

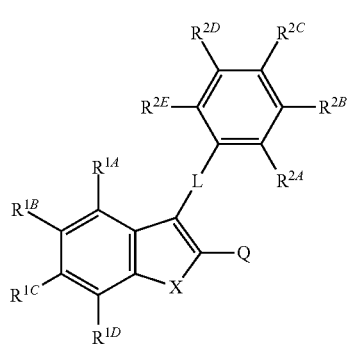

(I)

wherein:

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl, and wherein the method comprises determining a level of the biological marker in a sample obtained from the patient following administration with the vascular disrupting agent, wherein the sample is a tumor, blood, serum or plasma.

2. The method of claim 1, wherein the wherein the level of the biological marker is determined by measuring the level of biological marker polypeptide.

3. The method of claim 1, wherein the biological marker is selected from SAP, SHBG, and/or Myoglobin and the level of the biological marker is lower following administration with the vascular disrupting agent when compared to the level of the biological marker prior to administration with the vascular disrupting agent.

4. The method of claim 1, wherein the biological marker is SCF and the level of the biological marker is higher following administration with the vascular disrupting agent when compared to the level of the biological marker prior to administration with the vascular disrupting agent.

5. The method of claim 1, wherein the vascular disrupting agent is selected from 2-methyl-7-hydroxy-3-(3,4,5-trimethoxybenzoyl)-6-methoxybenzofuran and disodium [6-methoxy-2-methyl-3-(3,4,5-trimethoxybenzoyl)-1-benzofuran-7-yl] phosphate.

6. The method of claim 1, wherein the patient is a renal cancer patient.

7. The method of claim 1, comprising administering a further therapeutic agent and/or tumor irradiation to the patient.

8. The method of claim 7, wherein the further therapeutic agent is selected from a chemotherapeutic, an antibody and/or an immunotherapeutic.

9. The method of claim 7, wherein the further therapeutic agent is selected from an mTOR inhibitor, tyrosine kinase inhibitor and/or a VEGF inhibitor.

* * * * *